US011370816B2

(12) United States Patent
Aakalu

(10) Patent No.: US 11,370,816 B2
(45) Date of Patent: Jun. 28, 2022

(54) HISTATINS AND METHOD OF USE THEREOF

(71) Applicant: THE BOARD OF TRUSTEES OF THE UNIVERSITY OF ILLINOIS, Urbana, IL (US)

(72) Inventor: Vinay Aakalu, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/011,273

(22) Filed: Sep. 3, 2020

(65) Prior Publication Data

US 2020/0399333 A1 Dec. 24, 2020

Related U.S. Application Data

(63) Continuation of application No. 15/775,901, filed as application No. PCT/US2016/063906 on Nov. 29, 2016, now Pat. No. 10,800,822.

(60) Provisional application No. 62/260,705, filed on Nov. 30, 2015.

(51) Int. Cl.

| | |
|---|---|
| ***C07K 14/47*** | (2006.01) |
| ***A61K 38/00*** | (2006.01) |
| ***A61P 27/02*** | (2006.01) |
| ***A61K 38/17*** | (2006.01) |
| ***A61K 9/00*** | (2006.01) |
| ***A61K 38/06*** | (2006.01) |
| ***A61K 38/08*** | (2019.01) |
| ***A61K 38/12*** | (2006.01) |
| ***C12N 9/50*** | (2006.01) |

(52) U.S. Cl.

CPC .......... *C07K 14/4723* (2013.01); *A61K 38/00* (2013.01); *A61K 38/1709* (2013.01); *A61P 27/02* (2018.01); *A61K 9/0048* (2013.01); *A61K 9/0051* (2013.01); *A61K 38/06* (2013.01); *A61K 38/08* (2013.01); *A61K 38/12* (2013.01); *C12N 9/50* (2013.01)

(58) Field of Classification Search

CPC .... C07K 14/4723; A61P 27/02; A61K 9/0048

See application file for complete search history.

(56) References Cited

U.S. PATENT DOCUMENTS

| | | | | |
|---|---|---|---|---|
| 6,555,650 B1 * | 4/2003 | Lajoie | C07K 7/06 435/243 |
| 2009/0162437 A1 | 6/2009 | Horii | |
| 2010/0173833 A1 | 7/2010 | Lajoie | |
| 2010/0202983 A1 | 8/2010 | Jernberg | |
| 2011/0178010 A1 * | 7/2011 | Bolscher | A61K 38/1729 514/8.2 |
| 2013/0288964 A1 | 10/2013 | Bolscher | |
| 2013/0310326 A1 | 11/2013 | Sambursky | |
| 2013/0310327 A1 | 11/2013 | Sambursky | |
| 2016/0279194 A1 | 9/2016 | Sambursky | |

FOREIGN PATENT DOCUMENTS

| | | |
|---|---|---|
| WO | 2007142381 A1 | 12/2007 |
| WO | 2013173180 A2 | 11/2013 |
| WO | 2016060916 A1 | 4/2016 |
| WO | 2016060917 A2 | 4/2016 |
| WO | 2016060918 A2 | 4/2016 |
| WO | 2016060921 A1 | 4/2016 |

OTHER PUBLICATIONS

Chen et al. ("Fusion Protein Linkers: Property, Design and Functionality,"Adv Drug Deliv Rev. Oct. 15, 2013; 65(10): 1357-1369) (Year: 2013).*

Wu et al. ("Sortase A-catalyzed peptide cyclization for the synthesis of macrocyclic peptides and glycopeptides," Chem. Commun., 2011, 47, 9218-9220) (Year: 2011).*

Aakalu, et al (2014) "Accessory lacrimal gland (ALG) gene expression from human muller muscle conjunctival resection (MMCR) specimens obtained via laser capture microdissection (LCM)," Invest. Ophthalmol. Vis. Sci. 55:3115.

Bolscher et al. (2011) "Sortase A as a tool for high-yield histatin cyclization," FASEB J. 25:2650-2658.

Brewer & Lajoie (2002) "Structure-based design of potent histatin analogues," Biochemistry 41:5526-5536.

Brewer et al. (1998) "NMR studies of the antimicrobial salivary peptides histatin 3 and histatin 5 in aqueous and nonaqueous solutions," Biochem. Cell Biol. 76:247-256.

Chen et al. (2013) "Fusion protein linkers: Property, design and functionality," Adv. Drug Deliv. Rev. 65(10):1357-1369.

ExPasy Peptide Cutter Tool—result for sequence HEHEHKHKHEHEHKHK, downloaded Feb. 26, 2020.

Gusman et al. (2001) "Is salivary histatin 5 a metallopeptide?" Biochim. Biophys. Acta 1545:86-95.

International Preliminary Report on Patentability in PCT/US2016/063906 dated May 6, 2018.

International Search Report and Written Opinion in PCT/US2016/063906 dated Apr. 21, 2017.

Melino et al. (2014) "Histatins: salivary peptides with copper(II)- and zinc(II)-binding motifs: perspectives for biomedical applications," FEBS J. 281:657-672.

Melino et al. (1999) "Zn(2+)" ions selectively induce antimicrobial salivary peptide histatin-5 to fuse negatively charged vesicles. Identification and characterization of a zinc-binding motif present in the functional domain, Biochemistry 38:9626-9633.

(Continued)

*Primary Examiner* — Christina Bradley

(74) *Attorney, Agent, or Firm* — Licata & Tyrrell P.C.

(57) ABSTRACT

Synthetic histatins composed of combinations of functional domains of natural histatins separated by exogenous linkers are described as are methods of using endogenous and synthetic histatins for the treatment of ocular diseases or conditions.

28 Claims, 2 Drawing Sheets

Specification includes a Sequence Listing.

(56) References Cited

OTHER PUBLICATIONS

Office Communication dated Dec. 11, 2019 from U.S. Appl. No. 15/775,901, filed May 14, 2018.
Office Communication dated Mar. 3, 2020 from U.S. Appl. No. 15/775,901, filed May 14, 2018.
Oppenheim et al. (2012) "Anti-canadidal activity of genetically engineered histatin variants with multiple functional domains," PLoS ONE 7(12):251479.
Oudhoff et al. (2008) "Histatins are the major wound-closure stimulating factors in human saliva as identified in a cell culture assay," FASEB J. 22:3805-3812.
Oudhoff et al. (2009) "Histatins enhance wound closure with oral and non-oral cells," J. Dent. Res. 88:846-850.
Oudhoff et al. (2009) "Structure-activity analysis of histatin, a potent wound healing peptide from human saliva: cyclization of histatin potentiates molar activity 1,000-fold," FASEB J. 23:3928-3935.
Sakhuja et al. (2011) "Design and synthesis of spiro [indole-thiazolidine] spiro [indole-pyrans] as antimicrobial agents" Bioorg Med Chern Lett. 21:5465-5469.
Sikorska & Kamysz (2014) "Effect of head-to-tail cyclization on conformation of histatin-5" J. Pept. Sci. 20:952-957.
Steele et al. (2002) "Detection of Histatin 5 in Normal Human Schirmer Strip Samples by Mass Spectroscopy" Invest. Ophthalmol. Vis. Sci. 43:98.
Supplementary Partial European Search Report dated Jun. 19, 2019 for EP 16871334.5.
Ubels et al. (2012) "Gene expression in human accessory lacrimal glands of Wolfring" Invest. Ophthalmol. Vis. Sci. 53:6738-674.

* cited by examiner

HISTATINS AND METHOD OF USE THEREOF

INTRODUCTION

This application is a continuation of U.S. Ser. No. 15/775,901 filed May 14, 2018, which is the National Stage of International Application No. PCT/US2016/063906 filed Nov. 29, 2016, which claims benefit of priority to U.S. Provisional Patent Application Ser. No. 62/260,705, filed Nov. 30, 2015, the contents of which are incorporated herein by reference in their entirety.

This invention was made with government support under grant number 5K08EY024339 awarded by the National Institutes of Health. The government has certain rights in the invention.

BACKGROUND

Histatins (HTNs) are small histidine-rich cationic peptides found in saliva, as well as human lacrimal epithelium (Aakalu, et al. (2014) *Invest. Ophthalmol. Vis. Sci.* 55:3115; Ubels, et al. (2012) *Invest. Ophthalmol. Vis. Sci.* 53(11): 6738-47; Steele, et al. (2002) *Invest. Ophthalmol. Vis. Sci.* 43:98). Histatins range in size from 7 to 38 amino acid residues in length and represent a group of antimicrobial peptides with antibacterial properties and significant antifungal properties. In addition, histatins have been implicated in wound healing, metal ion chelation, anti-inflammatory effects and angiogenesis (Melino, et al. (2014) *FEBS J.* 281:657-72; Oudhoff, et al. (2008) *FASEB J.* 22(12):3805-12); Oudhoff, et al. (2009) *J. Dent. Res.* 88(9):846-50; WO 2007/142381). Structure-function studies have identified distinct N-terminal and C-terminal domains in both HTN1 and HTN3, which respectively contribute to the antimicrobial and wound healing properties (Melino, et al. (1999) *Biochemistry* 38:9626-33; Brewer, et al. (1998) *Biochem. Cell Biol.* 76:247-56; Gusman, et al. (2001) *Biochim. Biophys. Acta* 1545:86-95). In this respect, histatins, as well as fragments, multimers and combinations thereof, have been suggested for use in treating various conditions including ocular surface disease (US 2013/0310327; 2013/0310326; WO 2016/060916; WO 2016/060917; WO 2016/060918; WO 2016/060921; US 2016/0279194) and wounds (US 2013/0288964; US 2011/0178010).

Cyclic analogs of histatins have also been described. For example, U.S. Pat. No. 6,555,650 describes cyclic analogues of HTN5 with disulfide bridges that create a cyclic portion of from 5-16 of said amino acid units. In addition, head-to-tail cyclization of HTN5 has been shown to increase amphipathicity of the peptide without affecting its antimicrobial potency (Sikorska & Kamysz (2014) *J. Pept. Sci.* 20:952-7). Further, cyclization of histatin-1 has been shown to potentiate the molar activity approximately 1000-fold (Oudhoff, et al. (2009) *FASEB J.* 23:3928-35) and increases wound closure activity (Bolscher, et al. (2011) *FASEB J.* 25:2650-8). Moreover, cyclic analogs of histatin, with enhanced potency have been suggested for use in treating microbial infection (US 2010/0173833; Brewer & Lajoie (2002) *Biochemistry* 41:5526-5536).

SUMMARY OF THE INVENTION

This invention provides a synthetic histatin having the general structure:

$$[HTNF_1\text{-}L_1\text{-}HTNF_2\text{-}(L_2)_y]_x \quad \text{(Formula I)}$$

wherein i) $HTNF_1$ is a first histatin fragment ranging in length from 5 to 20 amino acids;

ii) $HTNF_2$ is a second histatin fragment ranging in length from 5 to 20 amino acids;

iii) $L_1$ is a first linker;

iv) $L_2$ is a second linker;

v) x=1 to 3; and vi) y=0 to 2;

wherein $HTNF_1$ and $HTNF_2$ are each independently the same or different and $L_1$ and $L_2$ are each independently the same or different. In one embodiment, $HTNF_1$ or $HTNF_2$ has an amino acid sequence of SNYLYDN (SEQ ID NO:1) or HEXXH (SEQ ID NO:2), wherein each X is independently a basic amino acid residue. In another embodiment, $L_1$ or $L_2$ is a flexible linker, rigid linker, in vivo cleavable linker, or a combination thereof. In some embodiments, the flexible linker is a hydrocarbon linker having, e.g., the structure —$(CH_2)_6$—, or a peptide linker having an amino acid sequence of $(GGGGS)_n$ (SEQ ID NO:3), KESGSVSSEQLAQFRSLD (SEQ ID NO:4), or EGKSSGSGSESKST (SEQ ID NO:5), GGGGGGGG (SEQ ID NO:6), GSAGSAAGSGEF (SEQ ID NO:7), $(GGSG)_n$ (SEQ ID NO:8), or $(GS)_n$ (SEQ ID NO:9), wherein n is 1-5. In other embodiments, the rigid linker is a peptide linker having an amino acid sequence of $(EAAAK)_n$ (SEQ ID NO:10), $A(EAAAK)_nA$ (SEQ ID NO:11), PAPAP (SEQ ID NO:12), or $(XP)_n$ (SEQ ID NO:13), wherein n is 1, 2, 3, 4 or 5. In yet another embodiment, the in vivo cleavable linker is a peptide linker having an amino acid sequence of VSQTSKLTRAETVFPDV (SEQ ID NO:14), PLGLWA (SEQ ID NO:15), RVLAEA (SEQ ID NO:16), EDVVCCSMSY (SEQ ID NO:17), GGIEGRGS (SEQ ID NO:18), TRHRQPRGWE (SEQ ID NO:19), AGNRVRRSVG (SEQ ID NO:20), RRRRRRRRR (SEQ ID NO:21), GFLG (SEQ ID NO:22), or CRRRRRREAEAC (SEQ ID NO:23). In still further embodiments, the synthetic histatin is linear or cyclized, e.g., via a disulfide bridge between terminal cysteine residues or with a sortase or butelase. In certain embodiments, the synthetic histatin has the structure:

GYKRKFHEKHHSHR (SEQ ID NO:24)-$L_1$-YGDYGSNYLYDN (SEQ ID NO:25);

HEKHH (SEQ ID NO:26)-$L_1$-HEKHH (SEQ ID NO:26)-$L_2$-HEKHH (SEQ ID NO:26)-$L_1$-YGDYGSNYLYDN (SEQ ID NO:25);

HEKRHH (SEQ ID NO:27)-$L_1$-HEKRHH (SEQ ID NO:27)-$L_2$-HEKRHH (SEQ ID NO:27)-$L_1$-YGDYGSNYLYDN (SEQ ID NO:25);

HEKRHH (SEQ ID NO:27)-$L_1$-HEKRHH (SEQ ID NO:27)-$L_2$-HEKHH (SEQ ID NO:26)-$L_1$-YGDYGSNYLYDN (SEQ ID NO:25); or

HEKRHH (SEQ ID NO:27)-$L_1$-HEKHH (SEQ ID NO:26)-$L_2$-HEKHH (SEQ ID NO:26)-$L_1$-YGDYGSNYLYDN (SEQ ID NO:25), wherein each $L_1$ and $L_2$ is independently a flexible linker, rigid linker, or in vivo cleavable linker. In specific embodiments, the synthetic histatin has the structure: GYKRKFHEKHHSHR-$(CH_2)_6$-YGDYGSNYLYDN (SEQ ID NO:28), HEKHH-$(CH_2)_6$-HEKHH-$(CH_2)_6$-HEKHH-$(CH_2)_6$-YGDYGSNYLYDN (SEQ ID NO:29), HEKRHH-$(CH_2)_6$-HEKRHH-$(CH_2)_6$-HEKRHH-$(CH_2)_6$-YGDYGSNYLYDN (SEQ ID NO:30), HEKRHH-$(CH_2)_6$-HEKRHH-$(CH_2)_6$-HEKHH-$(CH_2)_6$-YGDYGSNYLYDN (SEQ ID NO:31) or HEKRHH-$(CH_2)_6$-HEKHH-$(CH_2)_6$-HEKHH-$(CH_2)_6$-YGDYGSNYLYDN (SEQ ID NO:32).

A composition containing one or more synthetic histatins of Formula I and a pharmaceutically acceptable carrier or excipient is also provided as is a kit and methods for treating an ocular disease or condition or providing wound healing, antimicrobial, metal ion chelating, anti-inflammatory, anti-angiogenic, or matrix metalloproteinase inhibitory activity in a tissue or organ using one or more synthetic histatins of Formula I.

DETAILED DESCRIPTION OF THE INVENTION

Figure 1:
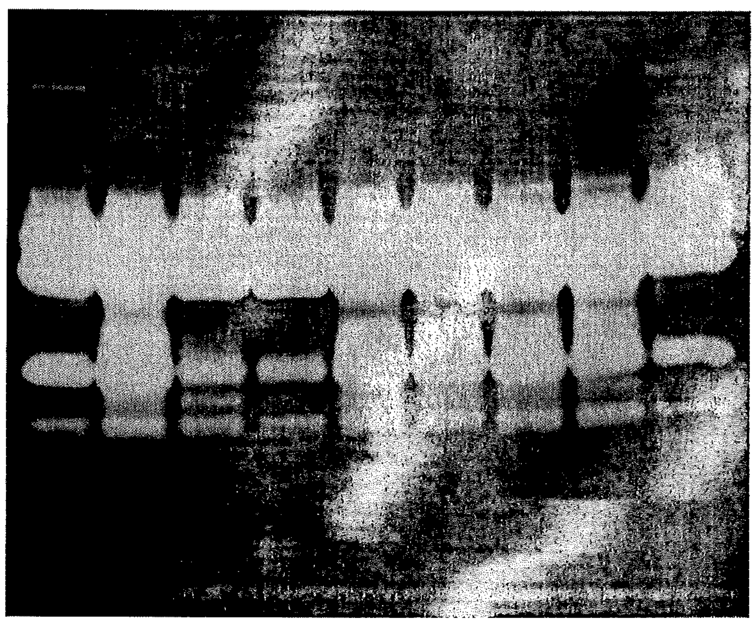
FIG. 1 show zymographic analysis of synthetic histatin inhibitory activity. Experiments included pro-MMP2 (100 ng; "−Ve"); activation of Pro-MMP2 with APMA (1 mM; "+Ve"); inclusion of a classic matrix metalloproteinase inhibitor, GM6001 (200 nM; "Inh"); and varying amounts of a synthetic histatin containing three metal binding domains from endogenous HTN5 and a wound healing domain from endogenous HTN1 ("H-1"). The protein ladder is shown on the right.

Histatins are appealing molecules for the development of ocular therapeutics because they are amphipathic, which is necessary for topical application and penetration into the eye, and promote wound healing through EGF-independent mechanisms. In addition, histatins promote wound healing without proliferation, inhibit MMP2/MMP9 and angiogenesis, prevent infection, and are anti-inflammatory. Corneal wounds, in particular, can cause vision loss primarily due to inflammatory scarring, and angiogenic vessel invasion. Utilizing histatin as a wound healing and anti-angiogenic agent has broad implication for ocular surface disease therapies. It has now been found that combinations of functional domains of histatin separated by exogenous linkers provide fusion peptides tailored for use in the treatment of human ocular disease. In particular, peptides composed of one or more zinc binding domains, with or without one or more wound healing domains, and with or without cyclization can be designed to manipulate the function and efficacy of histatin in various assays and applications.

Accordingly, this invention provides synthetic histatins and use of such peptides and/or endogenous histatins in antimicrobial, wound healing, metal ion chelating, anti-inflammatory, anti-cancer, anti-angiogenic, and/or matrix metalloproteinase inhibitory applications in particular in the treatment of an ocular disease or condition. In addition, novel uses of endogenous histatin peptides are provided including use in ocular surface disease, ocular neovascularization and dry eye disease. A synthetic histatin of this invention has the general structure:

$$[HTNF_1\text{-}L_1\text{-}HTNF_2\text{-}(L_2)_y]_x \quad \text{(Formula I)}$$

wherein i) $HTNF_1$ is a first histatin fragment ranging in length from about 5 to about 20 amino acids;

ii) $HTNF_2$ is a second histatin fragment ranging in length from about 5 to about 20 amino acids;

iii) $L_1$ is a first linker;

iv) $L_2$ is a second linker;

v) x=1 to 3; and vi) y=0 to 2;

wherein $HTNF_1$ and $HTNF_2$ are each independently the same or different and $L_1$ and $L_2$ are each independently the same or different.

The term "about" encompasses amounts that differ by ±1-2. Whether or not modified by the term "about", the claims include equivalents to the quantities. Where present, all ranges are inclusive and combinable. For example, when a range of "1 to 5" is recited, the recited range should be construed as including ranges "1 to 4," "1 to 3," "1-2," "1-2 & 4-5," "1-3 & 5," and the like.

A "histatin fragment" or "HTNF" refers to a fragment of a natural histatin. A "histatin fragment" or "HTNF" ranges in length from about 5 to about 20 amino acid residues and includes a metal binding domain, wound healing domain, or antimicrobial domain of a natural histatin. In certain embodiments, a histatin fragment is 5, 6, 7, 8, 9, 10, 11, 12, 13, 14, 15, 16, 17, 18, 19 or 20 amino acid residues in length. In other embodiments, a histatin fragment ranges in length from to 5 to 20 amino acid residues, 6 to 14 amino acid residues, or 12 to 14 amino acid residues.

In some embodiments, a synthetic histatin is composed of 2 HTNFs, i.e., x=1 and y=0. In other embodiments, a synthetic histatin is composed of 4 HTNFs, i.e., x=2 and y=1. In further embodiments, a synthetic histatin is composed of 6 HTNFs, i.e., x=3 and y=2. Larger synthetic histatin molecules including, e.g., 8, 10, 12, 14, 16 or more HTNFs, and those including, e.g., 3, 5, 7, 9, 11, 13, 15 or more HTNFs are also considered within the scope of this invention. However, it is desirable that the length the synthetic peptide is in the range of 20 to 50 amino acid residues. As used herein, "endogenous histatin," "native histatin" or "natural histatin" refers to a 7-44 amino acid residue, histidine-rich peptide, which was originally identified in saliva and characterized based upon its fungistatic effects. See, e.g., Melino, et al. (2014) *FEBS J.* 281:657-682, and references cited therein. Representative natural histatins include, but are not limited to, the peptides listed in Table 1.

TABLE 1

| Histatin | Sequence | SEQ ID NO: |
|---|---|---|
| HTN1 | DSpHEKRHHGYRRKFHEKHHSHREFPFYGDYGSNYLYDN | 33 |
| HTN2 | RKFHEKHHSHREFPFYGDYGSNYLYDN | 34 |
| HTN3 | DSHAKRHHGYKRKFHEKHHSHRGYRSNYLYDN | 35 |
| HTN4 | KFHEKHHSHRGYRSNYLYDN | 36 |
| HTN5 | DSHAKRHHGYKRKFHEKHHSHRGY | 37 |
| HTN6 | DSHAKRHHGYKRKFHEKHHSHRGYR | 38 |
| HTN7 | RKFHEKHHSHRGY | 39 |
| HTN8 | KFHEKHHSHRGY | 40 |
| HTN9 | RKFHEKHHSHRGYR | 41 |
| HTN10 | KFHEKHHSHRGYR | 42 |

TABLE 1-continued

| Histatin | Sequence | SEQ ID NO: |
|---|---|---|
| HTN11 | KRHHGYKR | 43 |
| HTN12 | KRHHGYK | 33 |
| HTN C-ter | YGDYGSNYLYDN | 25 |

"Sp" or "S(PO$_3$)" denotes phosphorylated serine.

The term "metal binding domain," as used herein, refers to an amino acid motif of natural histatin that binds or forms a complex with a metal. Structural and functional characterization of HTNs revealed the presence of two metal-binding motifs: the amino-terminal Cu(II)/Ni(II) binding (ATCUN) motif with one histidine residue in the third position ($NH_2$—$X_1X_2$H, wherein $X_1$ is Asp or Glu, and $X_2$ is Ala, Thr, Met or Ser) (Grogan, et al. (2001) *FEBS Lett.* 491:76-80; Melino, et al. (2006) *Biochemistry* 45:15373-83; Melino, et al. (1999) *Biochemistry* 38:9626-33; Gusman, et al. (2001) *Biochim. Biophys. Acta* 1545:86-95); and the Zn(II)-binding motif HEXXH (SEQ ID NO:2), wherein X denotes a basic amino acid residue such as Lys, Arg, or His. Accordingly, in some embodiments, the synthetic histatin includes an amino-terminal metal binding domain having the sequence DSH, ESH, DAH, EAH, DTH, ETH, DMH or EMH. In another embodiment, the synthetic histatin includes one or more metal binding domains having the sequence HEKKH (SEQ ID NO:45), HEKRH (SEQ ID NO:46), HEKHH (SEQ ID NO:26), HERKH (SEQ ID NO:47), HERRH (SEQ ID NO:48), HERHH (SEQ ID NO:49), HEHKH (SEQ ID NO:50), HEHRH (SEQ ID NO:51) or HEHHH (SEQ ID NO:52). $HTNF_1$ or $HTNF_2$ can include the specific sequence of the above-referenced metal binding domains or can include between 1 and 6 additional native histatin amino acid residues on the C- and/or N-terminus of the metal binding domain. By way of illustration, a HTNF with a metal binding domain can have the sequence GYKRKF<u>HEKHH</u>SHR (SEQ ID NO:24) or <u>HEKRH</u>H (SEQ ID NO:27)

In some embodiments, a synthetic histatin includes one metal binding domain, i.e., either $HTNF_1$ or $HTNF_2$ is a metal binding domain. In other embodiments, a synthetic histatin includes two metal binding domains. In further embodiments, a synthetic histatin includes three metal binding domains. In certain embodiments, a metal binding domain has the sequence DHX, wherein X is Ser. In other embodiments, a metal binding domain has the sequence HEXXH (SEQ ID NO:2), wherein each X is a basic amino acid residue. As would be readily appreciated by those of skill in the art, the inclusion of one or more metal binding domains in a synthetic histatin impart metal ion chelating, anti-inflammatory, matrix metalloproteinase inhibitory, and/or anti-angiogenic activity to the synthetic histatin. In light of its anti-angiogenic activity, such a synthetic and/or endogenous histatin would be of use in treating age-related macular degeneration, diabetic retinopathy, cancer, and chronic or acute sever uveitis. In light of its metal ion chelating activity, such a synthetic and/or endogenous histatin would also be of use in inhibiting tissue destruction mediated by matrix metalloproteinases and other metal-dependent enzymes in inflammatory and infectious diseases such as infectious keratitis, intraocular uveitis, endophthalmitis, inflammatory keratitis, dry eye disease and ocular surface or intraocular diseases.

As used herein, "wound healing domain" refers to an amino acid motif of natural histatin that promotes or facilitates wound healing. It has been reported that HTN1 and HTN3, but not HTN5, exhibit wound closure activities in vitro (Oudhoff, et al. (2008) *FASEB J.* 22:3805-3812). The inactivity of HTN5, which is composed of the N-terminal 22 amino acid residues of HTN1 and HTN3, indicates that the C-terminal residues in HTN1 and HTN3 are responsible for wound closure activity. Accordingly, for the purposes of this invention, a wound healing domain of natural histatin includes the sequence SNYLYDN (SEQ ID NO:1). $HTNF_1$ or $HTNF_2$ can include the specific sequence of the above-referenced wound healing domain or can include between 1 and 6 additional native histatin amino acid residues on the C- and/or N-terminus of the wound healing domain. By way of illustration, a HTNF with a wound healing domain can have the sequence GYKRKF<u>HEKHH</u>SHR (SEQ ID NO:24).

In some embodiments, a synthetic histatin includes one wound healing domain, i.e., $HTNF_1$ or $HTNF_2$ is a wound healing domain. In other embodiments, a synthetic histatin includes two wound healing domains. In further embodiments, a synthetic histatin includes three wound healing domains. As would be readily appreciated by those of skill in the art, the inclusion of one or more wound healing domains in a synthetic histatin impart epithelial cell migration and spreading activity to the synthetic histatin. Such a synthetic histatin would therefore be of use in wound healing as well as the treatment of retinal pigment epithelial healing, dry age-related macular degeneration, ocular surface diseases and ocular surface inflammatory disorders, ocular neovascularization including corneal and intraocular, retinal or choroidal, and dry eye diseases.

The term "antimicrobial domain," as used herein, refers to an amino acid motif of natural histatin that exhibits cytostatic or cytocidal activity toward bacterial and/or fungal cells. Characterization of HTNs indicates that a positive net charge and the amino-terminal portion of HTNs mediate antimicrobial activity. In particular, the amino acid sequence RKFHEKHHSHRGYR (SEQ ID NO:53) of HTN3 has been shown to exhibit fungicidal activity (Oppenheim, et al. (2012) *PLoS ONE* 7(12):e51479). Similarly, the sequence AKRHHGYKRKFH (SEQ ID NO:54), also known as P-113, exhibits fungicidal activity against *Candida albicans* (Jang, et al. (2008) *Antimicrob. Agents Chemother.* 5292):497-504). $HTNF_1$ or $HTNF_2$ can include the specific sequence of the above-referenced antimicrobial domains or can include between 1 and 6 additional native histatin amino acid residues on the C- and/or N-terminus of the wound healing domain.

In some embodiments, a synthetic histatin includes one antimicrobial domain, i.e., $HTNF_1$ or $HTNF_2$ is an antimicrobial domain. In other embodiments, a synthetic histatin includes two antimicrobial domains. In further embodiments, a synthetic histatin includes three antimicrobial domains. In certain embodiments, an antimicrobial domain has the sequence RKFHEKHHSHRGYR (SEQ ID NO:53). In other embodiments, an antimicrobial domain has the sequence AKRHHGYKRKFH (SEQ ID NO:54). As would be readily appreciated by those of skill in the art, the inclusion of one or more antimicrobial domains in a synthetic histatin impart antifungal and/or antibacterial activity to the synthetic histatin. Such a synthetic histatin would therefore be of use in treating microbial infections such as *Candida* eye infection as well as preventing infections associated with surgical implants.

Each of the individual histatin fragments, i.e., $HTNF_1$ and $HTNF_2$, of the synthetic histatin of this invention can be the same or different. In some embodiments, a synthetic histatin is composed of at least one metal binding domain and at least one wound healing domain. Accordingly, in embodiments of Formula I where x is 1 and y is 0, $HTNF_1$ is a metal binding domain and $HTNF_2$ is a wound healing domain. In embodiments of Formula I where x is 2 and y is 1, each $HTNF_1$ is a metal binding domain and each $HTNF_2$ is a wound healing domain. In other embodiments where x is 2 and y is 1, each $HTNF_1$ is a metal binding domain, one $HTNF_2$ is a metal binding domain and one $HTNF_2$ is a wound healing domain. In further embodiments, $HTNF_1$ and $HTNF_2$ are individually derived from the same or different natural histatins (i.e., HTN1-HTN12). For example, a synthetic histatin can be composed of one or more metal binding domains from HTN5 and a wound healing domain from HTN1. Alternatively, a synthetic histatin can be composed of one or more metal binding domains from HTN1 and a wound healing domain from HTN1. Examples of synthetic histatins containing combinations of metal binding domains and wound healing domains are presented in Table 2.

TABLE 2

| Synthetic Histatin |
|---|
| GYKRKFHEKHHSHR(SEQ ID NO: 24)-$L_1$-YGDYGSNYLYDN(SEQ ID NO: 25) |
| HEKHH(SEQ ID NO: 26)-$L_1$-HEKHH(SEQ ID NO: 26)-$L_2$-HEKHH(SEQ ID NO: 26)-$L_1$-YGDYGSNYLYDN(SEQ ID NO: 25) |
| HEKRHH(SEQ ID NO: 27)-$L_1$-HEKRHH(SEQ ID NO: 27)-$L_2$-HEKRHH(SEQ ID NO: 27)-$L_1$-YGDYGSNYLYDN(SEQ ID NO: 25) |
| HEKRHH(SEQ ID NO: 27)-$L_1$-HEKRHH(SEQ ID NO: 27)-$L_2$-HEKHH(SEQ ID NO: 26)-$L_1$-YGDYGSNYLYDN(SEQ ID NO: 25) |
| HEKRHH(SEQ ID NO: 27)-$L_1$-HEKHH(SEQ ID NO: 26)-$L_2$-HEKHH(SEQ ID NO: 26)-$L_1$-YGDYGSNYLYDN(SEQ ID NO: 25) |

As used herein, the terms "linker" or "spacer" refers to a heterologous molecule used to connect, link or join together two or more HTNFs. The term "heterologous molecule" refers to a molecule that is not normally found in a histatin or not typically disposed between the HTNF amino acid sequences in nature. As used herein, the term "linked," "joined" or "connected" generally refers to a functional linkage between two contiguous or adjacent amino acid sequences to produce a molecule that does not exist in nature. Generally, the linked amino acid sequences are contiguous or adjacent to one another and retain their respective operability and function when joined. The linkers may provide desirable flexibility to permit the desired expression, activity and/or conformational positioning of the synthetic histatin.

In some embodiments, a synthetic histatin is composed of 2 HTNFs and one linker, i.e., x=1 and y=0. In other embodiments, a synthetic histatin is composed of 4 HTNFs and three linkers, i.e., x=2 and y=1. In further embodiments, a synthetic histatin is composed of 6 HTNFs and five linkers, i.e., x=3 and y=2. However, it is contemplated that additional linkers can be used when more HTNFs are combined.

Linkers of use in the synthetic histatin of Formula I can be flexible, rigid, in vivo cleavable, or a combination thereof. In addition, linkers can be composed of amino acid residues (i.e., peptide linkers) or composed of chains of hydrocarbons (i.e., hydrocarbon linkers). Peptide linkers can be of any appropriate length to connect one or more HTNFs of interest and are preferably designed so as to allow the proper folding and/or function and/or activity of one or both of the HTNFs it connects. Thus, the linker peptide can have a length of no more than 3, no more than 5, no more than 10, no more than 15, no more than 20, no more than 25, no more than 30, no more than 35, no more than 40, no more than 45, no more than 50, no more than 55, or no more than 60 amino acids. In some embodiments, the linker peptide can have a length of at least 3, at least 4, at least 5, at least 6, at least 7, at least 8, at least 9, at least 10, at least 12, at least 15, at least 18, at least 20, at least 25, at least 30, at least 35, at least 40, at least 45, or at least 50 amino acids. In some embodiments, the linker includes at least 10 and no more than 60 amino acids, at least 10 and no more than 55 amino acids, at least 10 and no more than 50 amino acids, at least 10 and no more than 45 amino acids, at least 10 and no more than 40 amino acids, at least 10 and no more 35 amino acids, at least 10 and no more than 30 amino acids, at least 10 and no more than 25 amino acids, at least 10 and no more than 20 amino acids or at least 10 and no more than 15 amino acids.

A "flexible" linker refers to a hydrocarbon or peptide linker that does not have a fixed structure (secondary or tertiary structure) in solution. Such a flexible linker is therefore free to adopt a variety of conformations. Flexible linkers of use herein include hydrocarbon linkers and peptide linkers composed of small, non-polar (e.g., Gly) and/or polar (e.g., Ser or Thr) amino acid residues. Simple amino acids (e.g., amino acids with simple side chains (e.g., H, $CH_3$ or $CH_2OH$) are advantageous for use in a peptide linker as the lack of branched side chains on these amino acids provides greater flexibility (e.g., two-dimensional or three-dimensional flexibility) within the linker and, accordingly, within a polypeptide composition. The flexible linker may contain additional amino acids such as Thr and Ala to maintain flexibility, as well as polar amino acids such as Lys and Glu to improve solubility. The amino acids can alternate/repeat in any manner consistent with the linker remaining functional (e.g., resulting in expressed and/or active polypeptide(s)). Flexible linkers are described, for example, in Chen, et al. (2013) *Adv. Drug Deliv. Rev.* 65(10):1357-1369; US 2012/0232021; US 2014/0079701; WO 1999/045132; WO 1994/012520 and WO 2001/1053480.

In other embodiments, the flexible linker is a hydrocarbon linker. The hydrocarbon linking the HTNFs should have sufficient length and flexibility so that the synthetic histatin can achieve the desired conformation. In certain embodiments, the hydrocarbon is composed of one or more methylene (—$CH_2$—) groups. In certain embodiments, the hydrocarbon includes between 3 and 25 methylene groups, i.e., —$(CH_2)_n$—, wherein n is 3 to 25. In certain embodiments, the hydrocarbon linker has the structure —$(CH_2)_6$—. Additional carbon-based linkers such as glycol linkers could also be used in the synthetic histatin of this invention.

In other embodiments, the linker is a rigid linker. "Rigid" linker refers to a molecule that adopts a relatively well-defined conformation when in solution. Rigid linkers are therefore those which have a particular secondary and/or tertiary structure in solution. Rigid linkers are typically of a size sufficient to confer secondary or tertiary structure to the linker. Such linkers include aromatic molecules (see, e.g., U.S. Pat. Nos. 6,096,875 or 5,948,648), peptide linkers rich in proline, or peptide linkers having an inflexible helical structure. Rigid linkers are described in, for example, Chen, et al. (2013) *Adv. Drug Deliv. Rev.* 65(10):1357-1369; US 2010/0158823 and US 2009/10221477.

In other embodiments, the linker is an in vivo cleavable linker. In vivo cleavable linkers can include a cleavable disulfide bond formed between two cysteine residues or linkers having a protease recognition sequence, e.g., recognized by matrix metalloproteases (MMPs).

Examples of suitable peptide linkers of use in the synthetic histatin are provided in Table 3.

TABLE 3

| Type | Sequence | SEQ ID NO: |
|---|---|---|
| Flexible | $(GGGGS)_n$ | 3 |
| Flexible | KESGSVSSEQLAQFRSLD | 4 |
| Flexible | EGKSSGSGSESKST | 5 |
| Flexible | GGGGGGGG | 6 |
| Flexible | GSAGSAAGSGEF | 7 |
| Flexible | $(GGSG)_n$ | 8 |
| Flexible | $(GS)_n$ | 9 |
| Rigid | $(EAAAK)_n$ | 10 |
| Rigid | $A(EAAAK)_nA$ | 11 |
| Rigid | PAPAP | 12 |
| Rigid | $(XP)_n$ | 13 |
| Cleavable | VSQTSKLTRAETVFPDV | 14 |
| Cleavable | PLGLWA | 15 |
| Cleavable | RVLAEA | 16 |
| Cleavable | EDVVCCSMSY | 17 |
| Cleavable | GGIEGRGS | 18 |
| Cleavable | TRHRQPRGWE | 19 |
| Cleavable | AGNRVRRSVG | 20 |
| Cleavable | RRRRRRRRR | 21 |
| Cleavable | GFLG | 22 |
| Cleavable | CRRRRRREAEAC | 23 |

n is 1 to 5. X may be any amino acid residue, but is preferably Ala, Lys or Glu.

Each of the individual linkers, i.e., $L_1$ and $L_2$, of the synthetic histatin of this invention can be the same or different. In some embodiments, a synthetic histatin includes at least one flexible linker. In some embodiments, at least one flexible linker is a hydrocarbon linker. In other embodiments, at least one flexible linker is a peptide linker. In particular embodiments, each linker, i.e., $L_1$ and $L_2$, of the synthetic histatin is a hydrocarbon linker. In certain embodiments, each linker, i.e., $L_1$ and $L_2$, of the synthetic histatin has the structure $—(CH_2)_6—$.

Examples of synthetic histatins containing combinations of metal binding domains and wound healing domains with flexible linkers are presented in Table 4.

TABLE 4

| Synthetic Histatin | SEQ ID NO: |
|---|---|
| GYKRKFHEKHHSHR-$(CH_2)_6$-YGDYGSNYLYDN | 28 |
| HEKHH-$(CH_2)_6$-HEKHH-$(CH_2)_6$-HEKHH-$(CH_2)_6$-YGDYGSNYLYDN | 29 |
| HEKRHH-$(CH_2)_6$-HEKRHH-$(CH_2)_6$-HEKRHH-$(CH_2)_6$-YGDYGSNYLYDN | 30 |
| HEKRHH-$(CH_2)_6$-HEKRHH-$(CH_2)_6$-HEKHH-$(CH_2)_6$-YGDYGSNYLYDN | 31 |
| HEKRHH-$(CH_2)_6$-HEKHH-$(CH_2)_6$-HEKHH-$(CH_2)_6$-YGDYGSNYLYDN | 32 |

The synthetic histatins described herein are commonly referred to as fusion or chimeric polypeptides. Such molecules can be synthesized by routine methods including recombinant protein expression, chemical synthesis, or a combination thereof. In some embodiments, the synthetic histatin of the invention is synthesized recombinantly using recombinant DNA techniques. Thus, the invention provides polynucleotides that encode the synthetic histatin of the invention. In a related aspect, the invention provides vectors, particularly expression vectors that harbor the polynucleotides encoding the synthetic histatin of the invention. In certain embodiments, the vector provides replication, transcription and/or translation regulatory sequences that facilitate recombinant synthesis of the desired synthetic histatin in a eukaryotic cell or prokaryotic cell. Accordingly, the invention also provides host cells for recombinant expression of the synthetic histatin and methods of harvesting and purifying the synthetic histatin produced by the host cells. Production and purification of recombinant peptides is a routine practice to one of skilled in the art and any suitable methodology can be used.

In another embodiment, the synthetic histatin is synthesized by any of the chemical synthesis techniques known in the art, particularly solid-phase synthesis techniques, for example, using commercially-available automated peptide synthesizers. See, for example, Stewart & Young (1984) *Solid Phase Peptide Synthesis,* $2^{nd}$ ed., Pierce Chemical Co.; Tarn, et al. (1983) *J. Am. Chem. Soc.* 105:6442-55; Merrifield (1986) *Science* 232:341-347; and Barany et al. (1987) *Int. J. Peptide Protein Res.* 30:705-739.

The synthetic histatin can be isolated and/or purified by any suitable methods known in the art including without limitation gel filtration and affinity purification. In some embodiments, the synthetic histatin is produced with a tag, e.g., an epitope tag, to facilitate isolation of the synthetic histatin. In one aspect, the synthetic histatin is at least 1% pure, e.g., at least 5% pure, at least 10% pure, at least 20% pure, at least 40% pure, at least 60% pure, at least 80% pure, and at least 90% pure, as determined by SDS-PAGE. Once isolated and/or purified, the properties of the synthetic histatin can be readily verified by techniques known to those skilled in the art.

While the HTN fragments disclosed herein are derived from human sequences, orthologs or allelic variants of the HTN fragments can also be used. The term "ortholog" refers to the same protein in another species (e.g., *Macaca fascicularis, Trachypithecus cristatus, Chlorocebus aethiops, Nomascus leucogenys*, or *Gorilla gorilla*), which exhibits the same activity. By comparison, "allelic variant" refers the same protein in the same species, which may have an altered amino acid sequence resulting from a polymorphism within the population. In certain embodiments, the HTN fragment ortholog or allelic variant has sequence identity of at least 80%, at least 85%, at least 90%, at least 95%, at least 96%, at least 97%, at least 98%, or at least 99%, but less than 100%, to the HTN fragments disclosed herein.

Derivatives and analogs of the synthetic histatins described herein are all contemplated and can be made by altering their amino acid sequences by substitutions, additions, and/or deletions/truncations or by introducing chemical modifications that result in functionally equivalent molecules. It will be understood by one of ordinary skill in the art that certain amino acids in a sequence of any polypeptide may be substituted for other amino acids without adversely affecting the activity of the polypeptides.

In certain embodiments, the synthetic histatins of the invention include one or more modifications including without limitation phosphorylation, glycosylation, hydroxylation, sulfonation, amidation, acetylation, carboxylation, palmitoylation, PEGylation, introduction of nonhydrolyzable bonds, and disulfide formation. The modification may improve the stability and/or activity of the synthetic histatins.

For example, the C-terminal may be modified with amidation, addition of peptide alcohols and aldehydes, addition of esters, or addition of p-nitroaniline and thioesters. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g., lipopeptides), biotinylation, phosphorylation, sulfation, glycosylation, introduction of maleimido group, chelating moieties, chromophores or fluorophores.

In one embodiment, the synthetic histatin is conjugated to a fatty acid, e.g., the synthetic histatin is myristoylated. For example, a fatty acid may be conjugated to the N-terminus of the synthetic histatin. Such fatty acids include caprylic acid, capric acid, lauric acid, myristic acid, palmitic acid, stearic acid, etc. Furthermore, cysteines in synthetic histatin can be palmitoylated. In one embodiment, the synthetic histatin is myristylated, stearylated or palmitoylated at the N terminal amino acid.

In addition, or as an alternative, to post-translational modifications, the synthetic histatin can be conjugated or linked to another peptide, such as a carrier peptide. The carrier peptide may facilitate cell-penetration and can include peptides such as antennapedia peptide, penetratin peptide, TAT, transportan or polyarginine. In an embodiment, the peptide is conjugated or linked to the antennapedia peptide, RQIKIWFQNRRMKWKK (SEQ ID NO:55).

A synthetic histatin of the invention may also be cyclized. As used herein the term “cyclized” or “cyclic” denote an analog of a linear peptide that incorporates at least one bridging group (e.g., an amide, thioether, thioester, disulfide, urea, carbamate, hydrocarbon or sulfonamide) between to amino acid residues to form a cyclic structure. The bridging group can present on the side chain of an amino acid residue or a terminal amino acid residue thereby providing side chain cyclization (e.g., lactam bridge, thioester), head-to-tail cyclization, or hydrocarbon-stapled peptides.

In certain embodiments, the cyclic synthetic histatin has a disulfide bridge between two terminal cysteine residues. Representative amino acid sequences for preparing cyclized synthetic histatins are provided in Table 5.

TABLE 5

| Cyclic Synthetic Histatin | SEQ ID NO: |
|---|---|
| CGYKRKFHEKHHSHR-$(CH_2)_6$-YGDYGSNYLYDNC | 56 |
| CHEKHH-$(CH_2)_6$-HEKHH-$(CH_2)_6$-HEKHH-$(CH_2)_6$-YGDYGSNYLYDNC | 57 |
| CHEKRHH-$(CH_2)_6$-HEKRHH-$(CH_2)_6$-HEKRHH-$(CH_2)_6$-YGDYGSNYLYDNC | 58 |
| CHEKRHH-$(CH_2)_6$-HEKRHH-$(CH_2)_6$-HEKHH-$(CH_2)_6$-YGDYGSNYLYDNC | 59 |
| CHEKRHH-$(CH_2)_6$-HEKHH-$(CH_2)_6$-HEKHH-$(CH_2)_6$-YGDYGSNYLYDNC | 60 |

In other embodiments, the cyclic synthetic histatin is prepared from a linear peptide by cyclization with sortase. “Cyclization with sortase” or “cyclized with sortase” refers to a method of cyclizing a linear peptide using the enzyme sortase. Sortase-based cyclization is known in the art for manufacturing large cyclic peptides. See, Bolscher, et al. (2011) *FASEB J.* 25(8):2650-2658, and references cited therein.

Butelase cyclization has also been used to cyclize histatin. Addition of the tripeptide Asn-His-Val motif at the C-terminus provides a substrate for butelase to cyclize the synthetic histatin at a rate significantly faster than that of sortase A. See, Nguyen, et al. (2016) *Nat. Protocols* 11:1977-88; Tam, et al. (June 2015) *Peptides* 2015*: Proc.* 24*th* *Am. Pept. Symp.,* Orlando, Fla., pg. 27.

One of skill in the art will recognize that the synthetic histatin of the invention will be beneficial for treating diseases. Accordingly, to facilitate administration, this invention also provides a composition containing one or more endogenous and/or synthetic histatins and a pharmaceutically acceptable carrier or excipient. The pharmaceutical compositions provided herein can be formulated for oral, intravenous, intraperitoneal, intracerebral (intra-parenchymal), intracerebroventricular, intramuscular, intra-ocular, intraarterial, intraportal, intralesional or topical administration. Suitable pharmaceutical compositions can be determined by one skilled in the art depending upon, for example, the intended route of administration, delivery format and desired dosage. See, for example, Remington's Pharmaceutical Sciences (19th edition, 1995).

The endogenous and/or synthetic histatin(s) can be incorporated in a conventional systemic dosage form, such as a tablet, capsule, soft gelatin capsule, elixir or injectable formulation. The dosage forms may also include the necessary physiologically acceptable carrier material, excipient, lubricant, buffer, surfactant, antibacterial, bulking agent (such as mannitol), antioxidants (ascorbic acid or sodium bisulfite) or the like.

Acceptable formulation materials preferably are, nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS, PEG, sorbitan esters, polysorbates such as polysorbate 20 and polysorbate 80, TRITON, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, Remington's Pharmaceutical Sciences, Id.

The primary carrier or excipient in a pharmaceutical composition may be either aqueous or nonaqueous in nature. For example, a suitable carrier or excipient may be water for injection, physiological saline solution or artificial cerebrospinal fluid, possibly supplemented with other materials common in compositions for parenteral administration. Neutral buffered saline or saline mixed with serum albumin are further exemplary excipients. Pharmaceutical compositions can include Tris buffer of about pH 7.0-8.5, or acetate buffer of about pH 4.0-5.5, which may further include sorbitol or a suitable substitute. Pharmaceutical compositions of the invention may be prepared for storage by mixing the selected composition having the desired degree of purity with optional formulation agents (Remington's Pharmaceutical Sciences, Id.) in the form of a lyophilized cake or an aqueous solution. Further, the endogenous or synthetic histatins of the invention may be formulated as a lyophilizate using appropriate excipients such as sucrose.

Administration routes for the pharmaceutical compositions of the invention include the oral route; injection by intravenous, intraperitoneal, intracerebral (intra-parenchymal), intracerebroventricular, intramuscular, intra-ocular, intraarterial, intraportal, or intralesional routes; or via sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the synthetic histatin(s) has been absorbed or encapsulated. Where an implantation device is used, the device may be implanted into any suitable tissue or organ, and delivery of the endogenous or synthetic histatin(s) may be via diffusion, timed-release bolus, or continuous administration.

When parenteral administration is contemplated, the compositions for use in this invention may be in the form of a pyrogen-free, parenterally acceptable aqueous solution containing the endogenous or synthetic histatin(s) of the invention in a pharmaceutically acceptable vehicle. A particularly suitable vehicle for parenteral injection is sterile distilled water in which the endogenous or synthetic histatin(s) is formulated as a sterile, isotonic solution, appropriately preserved. Preparation can involve the formulation of the synthetic histatin(s) with an agent, such as injectable microspheres, bio-erodible particles, polymeric compounds (such as polylactic acid or polyglycolic acid), beads or liposomes, that may provide controlled or sustained release of the synthetic histatin(s), which may then be delivered via a depot injection. In particular, formulation with hyaluronic acid has the effect of promoting sustained duration in the circulation.

The compositions may also be formulated for inhalation. In these embodiments, the endogenous or synthetic histatin(s) of the invention is formulated as a dry powder for inhalation, or inhalation solutions may also be formulated with a propellant for aerosol delivery, such as by nebulization. Pulmonary administration is further described in, e.g., WO 1994/020069.

The pharmaceutical compositions of the invention can be delivered through the digestive tract, such as orally. The preparation of such pharmaceutically acceptable compositions is within the skill of the art. The endogenous or synthetic histatin(s) of the invention that is administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the endogenous or synthetic histatin(s). Diluents, flavorings, low melting point waxes, vegetable oils, lubricants, suspending agents, tablet disintegrating agents, and binders may also be used.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of an injectable pharmaceutical form can be brought about by the inclusion of agents which delay absorption such as aluminum monostearate and gelatin.

In certain embodiments, the endogenous or synthetic histatin(s) is formulated for treating ocular diseases or conditions, both on the surface and inside the eye. In particular embodiments, the endogenous or synthetic histatin(s) of the invention may be formulated and administered to the eye in drop form; topical gel form; as a solid formulation (e.g., similar to LACRISERT, hydroxypropyl cellulose ophthalmic insert); by injection into the anterior chamber of the eye; by injection into posterior chamber of the eye for inhibition of angiogenesis, inhibition of destructive MMP activity or to enhance epithelial wound healing; by coating of surgical devices (intraocular lens, glaucoma device, keratoprosthetic, lacrimal intubation tubes, lacrimal bypass tubes); by coating of contact lenses; or by coating of microbeads, nanobeads or other similar constructs.

As one skilled in the art will also appreciate, the composition described herein can be formulated so as to carry a minimum of adverse side effects. The compositions described herein can be suitable for long term use alone; useful as an adjunct therapy along with NSAIDS, glucocorticoids, immunosuppressive agents or anti-angiogenic agents; and/or useful in a program involving rotation between any or all of these agents, thereby decreasing long term exposure to (and, therefore, side effects resulting from) any one agent.

This invention also provides kits containing one or more of the endogenous or synthetic histatins, or a pharmaceutical composition containing the same, and optionally one or more NSAIDS, glucocorticoids, immunosuppressive agents or anti-angiogenic agents. Kits are typically provided in a suitable container (e.g., for example, a foil, plastic, or cardboard package). In certain embodiments, a kit may include one or more pharmaceutical excipients or carriers, pharmaceutical additives, and the like, as is described herein. In other embodiments, a kit may include a means for proper administration, such as, for example, graduated cups, syringes, needles, cleaning aids, an intraocular lens, a glaucoma device, an orbital implant, keratoprosthetic, lacrimal intubation tubes, lacrimal bypass tube, a contact lens and the like. In certain embodiments, a kit may include instructions for proper administration and/or preparation for proper administration.

Given the antimicrobial, wound healing, metal ion chelating, anti-inflammatory, anti-cancer, anti-angiogenic, and matrix metalloproteinase inhibitory applications of histatins, this invention also provides methods of treating a subject having a disease or condition for which histatins would provide a benefit. In accordance with such methods, a subject is administered one or more the synthetic histatins and/or endogenous histatins of this invention in an amount effective to treat the disease or condition. "Subject," as used herein, is meant to include humans, as well as non-human animals, particularly those who suffer from or who are susceptible to developing one or more of the disease or conditions described herein.

As used herein, the term "effective amount" or "therapeutically effective amount" refers to an amount of an endogenous or synthetic histatin of the invention or a pharmaceutical composition containing the endogenous or synthetic histatin sufficient to achieve the stated desired result. The amount of the peptide which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 μg/kg to up to about 100 mg/kg or more, depending on the factors mentioned above. In certain embodiments, the dosage may range from 0.1 μg/kg up to about 100 mg/kg, or 1 μg/kg up to about 100 mg/kg, or 5 μg/kg up to about 100 mg/kg.

"Treating" a subject having a disease or condition means accomplishing one or more of the following: (a) reducing the severity of the disease or condition; (b) arresting the development of the disease or condition; (c) inhibiting worsening of the disease or condition; (d) limiting or preventing recurrence of the d disease or condition in patients that have previously had the disease or condition; (e) causing regression of the disease or condition; (f) improving or eliminating the symptoms of the disease or condition; and/or (g) improving survival. As such, the treatment methods of this invention encompass both therapeutic and prophylactic administration.

In accordance with this invention, endogenous or synthetic histatins are of particular use in the treatment of ocular diseases or conditions including, but not limited to, ocular surface inflammatory disorders such as lupus, rheumatoid arthritis, corneal inflammation (e.g., Mooren's or inflammatory and infectious ulcerations), necrotizing scleritis, sarcoidosis or Wegener's disease; age-related macular degeneration (wet or dry); diabetic retinopathy; chronic or acute severe uveitis; retinal pigment epithelial disorders, e.g., hereditary disorders such as retinitis pigmentosa as well as non-hereditary retinal degenerations; ocular surface diseases mediated by inflammation, e.g., dry eye disease, graft versus host disease, Stevens-Johnson syndrome, alkali burns, and chronic atopic diseases such as atopic or allergic conjunctivitis or eczematous diseases; fungal and bacterial infection; corneal and conjunctival wounds, in particular wounds associated with neurotrophic/diabetic neuropathy. As a result of endogenous or synthetic histatin administration, corneal and scleral damage and melting are decreased and the activity of endogenous or environmental inflammatory agents, e.g., LPS (bound by histatin) are reduced.

In addition to the treatment of ocular diseases or conditions, the endogenous or synthetic histatins can be tailored to promote wound healing, and/or provide antimicrobial, metal ion chelating, anti-inflammatory, anti-angiogenic, and/or matrix metalloproteinase inhibitory activity in other tissues or organs of interest. In one embodiment, lamellar tissues, nerve tissues, connective tissues, vascular tissues, muscle tissues, skeletal tissues, or blood components are treated. In another embodiment, organs such as skin, liver, lung, kidney, heart, or bowel are treated. Treatment of such tissues and organs with an endogenous or synthetic histatin may provide benefit for subjects with wounds, infection, inflammatory and/or degenerative conditions such as atherosclerosis and arteriosclerosis, osteoarthritis and other degenerative joint diseases, optic atrophy, muscular dystrophy, degenerative processes associated with aging, asthma, dermatitis, laminitis, reactive airway disease, inflammatory bowel disease, multiple sclerosis, periodontal disease, psoriasis, type I diabetes, and ischemia-reperfusion injury.

The following non-limiting examples are provided to further illustrate the present invention.

Example 1: Histatin Synthesis and Purification

Linear peptide was synthesized using the stepwise solid-phase method by the 9-fluorenylmethoxycarbonyl (Fmoc) chemistry on the Wang resin (AnaSpec, Fremont, Calif.) with a 12 channel multiplex peptide synthesizer (Protein Technologies, Tucson, Ariz.) according to the manufacturer's procedures. Peptide synthesis started from the C-terminus of the peptide. The Fmoc group of the resin was removed with 20% piperidine in N,N-dimethylformamide (DMF) (5 min, ×2) followed by washing the resin with DMF (30 sec, 6×) before the amino acid (Fmoc protected, 2 equiv) was added in the presence of 0.2 M 2-(1H-Benzotriazole-l-yl)-1,1,3,3,-tetramethyluronium hexafluorophosphate (HBTU, 1.9 equiv) and 0.4 M 4-methylmorpholine (NMM, 4 equiv) in DMF (30 min, ×3). Excess reagents were washed away (30 sec, 6×) with DMF. The process was repeated until the last amino acid was added. After completion, the N-terminal Fmoc was removed with 20% piperidine in DMF (5 min, ×2) followed by washing the resin with DMF (30 sec, 6×). Detachment of peptide from the resin and removal of the side chain protection groups were done by incubating the resin with trifluoroacetic acid (TFA):Thioanisole:Water:Phenol:1,2-ethanedithio (82.5:5:5:5:2.5 v/v) cocktail for 2 hours. The reaction mixture was filtered followed by washing the resin with TFA (2×). Ice-cold ethyl ether was added to precipitate the peptide and the pellet was washed 2 times with ice-cold ethyl ether. The crude peptide was then dissolved in 50% acetonitrile in water and lyophilized.

The crude peptide was purified on a preparative KINETEX reversed-phase C18 column, 150×21.1 mm (Phenomenex, Torrance, Calif.) using a BIOCAD SPRINT HPLC system (Applied Biosystems, Foster City, Calif.). A flow rate of 30 mL/min with solvent A (0.1% TFA in deionized water) and solvent B (0.1% TFA in acetonitrile) was used. The column was equilibrated with 5% solvent B before sample injection. Elution was performed with a linear gradient from 5% solvent B to 100% solvent B in 60 min. The absorbance of the column effluent was monitored at 214 nm, and peak fractions were pooled and lyophilized. The pure peptide fraction was identified by matrix-assisted laser desorption/ionization time-of-flight mass spectrometry (MALDI-TOF MS) or electrospray ionization mass spectrometry (ESI MS) and lyophilized.

Example 2: Matrix Metalloproteinase Inhibition

Zymography analysis of a synthetic histatin containing three metal binding domains from HTN5 and one wound healing domain (i.e., SEQ ID NO:29) was carried out using conventional methods. See, e.g., Thomadaki, et al. (2013) *Oral Dis.* 19(8):781-8. This analysis demonstrated that the synthetic histatin inhibited MMP2 activity in a dose-dependent manner. See FIG. 1.

Example 3: Wound Healing Activity

A conventional in vitro scratch assay was used to measure cell migration in the presence of a synthetic histatin containing three metal binding domains from HTN5 and one wound healing domain (i.e., SEQ ID NO:29). A "scratch" was made in a monolayer of human corneal epithelium cells and time lapsed microscopy was used to capture images at the beginning and at regular intervals during cell migration to close the scratch. The results of this analysis indicated a notable enhancement of wound healing as evidenced by a reduction in time to wound closure (Table 6).

TABLE 6

| Amount of Synthetic Histatin | Time to Closure |
|---|---|
| Control (0 μM) | No closure in 48 hours |
| 1 μM | 48 hours |
| 10 μM | 22 hours |

Example 4: Anti-Angiogenesis Activity

Figure 2:
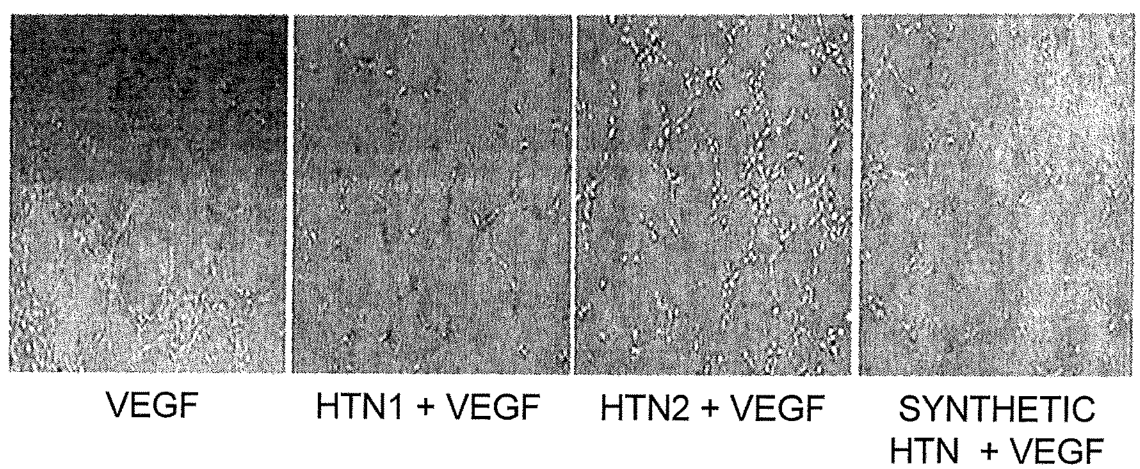
FIG. 2 shows VEGF-dependent inhibition of angiogenesis by endogenous HTN1, endogenous HTN2 and a synthetic histatin.

Tube formation assays were used to assess the anti-angiogenic property of synthetic histatin compared to native HTN1 and HTN2. Human umbilical vein endothelial cells (HUVECs) were suspended in diluted MATRIGEL for an overnight incubation and then subjected to a media change containing VEGF (10 ng/mL) (Goodwin (2007) *Microvasc. Res.* 74:172-83) alone or VEGF (10 ng/mL) in combination with HTN1, HTN2 or synthetic histatin (50 μM). While capillary-like structures were apparent when cells were treated with VEGF only, cells treated with synthetic histatin did not form such structures (FIG. 2).

Example 5: Changes in Gene Expression

Pathophysiological analyses of dry eye disease indicate that the critical factors involved in the development of dry eye disease involve inflammatory pathways including Th17/IL-17, I-CAM, IL-8, TNFα/IL-1/IL-6/NFκB, IL-10, MMP9 (and other matrix metalloproteinases) and TLR4/HSP (Stevenson, et al. (2012) *Arch. Ophthalmol.* 130(1):90-100). In addition, it has been reported that Ephrin A is involved in the development of epitheliopathy, poor wound healing and corneal disease related to elevated sugar levels/diabetic and neuropathic ulcers of the ocular surface. Accordingly, it was determined what effect synthetic histatin application would have on the gene expression in human corneal epithelium. With regard to inflammatory pathways, this analysis indicated that 7 of the 44 genes in the Th17/IL-17 pathway exhibited significant changes in gene expression in response to synthetic histatin treatment. Th17/IL-17 pathway is a central and important pathway in dry eye disease (Stevenson, et al. (2012) *Arch Ophthalmol.* 130(1):90-100).

Further, a 333% reduction in I-CAM gene expression and 400% reduction in the levels of IL-8 were observed. Moreover, 6 of the 62 genes in the IL-10 pathway were directed affected and 5 of 54 genes in the TLR4/HSP pathway were significantly affected. In addition, expression of several members of the TNFα/IL-1/IL-6/NFKB pathway were significant reduced and expression of genes related to MMP activity were reduced. These gene expression changes demonstrate the reduction in expression of inflammatory genes strongly associated with dry eye disease and ocular inflammatory diseases. Consistent with an improvement in corneal epithelial migration, path finding, cell spreading and wound closure, a 260% reduction in levels of Ephrin A was observed in response to synthetic histatin treatment.

Example 6: Treatment of Dry Eye Disease

Histatins are a histidine rich family of proteins which have primarily been found in saliva. These endogenous proteins (see Table 1), in addition to the synthetic histatins described herein, may have a number of therapeutic applications through a number of different means of delivery (e.g., topical, systemic, injected, carried on delivery materials). Such applications may include enhancement of ocular surface wound healing, prevention of ocular surface or intraocular inflammation and angiogenesis and prevention or treatment of dry eye diseases (inflammatory or otherwise).

Dry eye is a multifactorial disorder of the tears and ocular surface that results in symptoms of discomfort, visual disturbance, and tear film instability, with potential damage to the ocular surface. It is accompanied by increased osmolarity of the tear film and inflammation of the ocular surface (Lemp (1995) *CLAO J.* 21:221-2). For a more detailed definition, see "The definition and classification of dry eye disease: report of the Definition and Classification Subcommittee of the International Dry Eye WorkShop" (2007) *Ocul. Surf.* 5(2):75-9.

Figure 3:
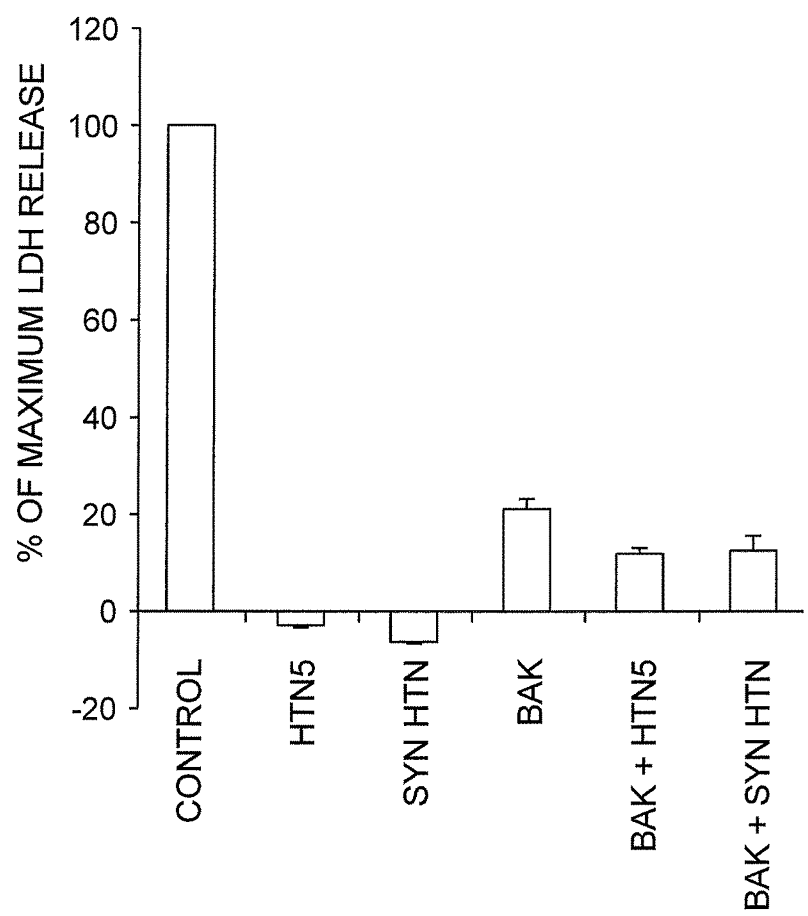
FIG. 3 shows the released amount of lactate dehydrogenase (LDH) from human corneal epithelial cells treated with 0.002% benzalkonium chloride (BAK), or native histatin (HTN5) or synthetic HTN (SYN HTN) in the presence or absence of BAK. Columns represent the mortality (mean±SD) of cells, total cellular death being 100% (Control).

One particularly useful model of dry eye disease and inflammatory ocular disease is the use of benzalkonium chloride (BAK) to induce cell death, inflammation and injury to ocular surfaces and corneal cells (Tressler, et al. (2011) *Ocul. Surf.* 9:140-58; Paimela, et al. (2012) *Mol. Vis.* 18:1189-1196). Briefly, human corneal epithelial cells were cultured under standard conditions. Cells were treated with native HTN5 (50 μM) or synthetic histatin (10 μM) in the presence or absence of 0.002% BAK. The permeability of cellular membranes following the exposures was determined by measuring the amount of released lactate dehydrogenase (LDH) enzyme from the cells. Maximum LDH release of cells was determined by lysing cells, and subsequently measuring the LDH from the culture medium. As shown in FIG. 3, topical HTN5 and synthetic histatin provided a statistically significant reduction in cell death. Accordingly, endogenous and synthetic histatins could be used to protect cells from injury, inflammation and cell death and are therefore of use in the treatment of dry eye disease.

What is claimed is:

1. A method of treating an ocular disease or condition comprising administering to a subject in need of treatment an effective amount of a synthetic histatin having the general structure:

$$[HTNF_1\text{-}L_1\text{-}HTNF_2\text{-}(L_2)_y]_x \quad \text{(Formula I)}$$

wherein i) $HTNF_1$ is a first histatin fragment ranging in length from 5 to 20 amino acids;

ii) $HTNF_2$ is a second histatin fragment ranging in length from 5 to 20 amino acids;

iii) $L_1$ is a first linker;

iv) $L_2$ is a second linker;

v) x=1 to 3; and vi) y=0 to 2;

wherein $HTNF_1$ and $HTNF_2$ are each independently the same or different and at least one of $L_1$ or $L_2$ is a hydrocarbon linker, thereby treating the subject's ocular disease or condition.

2. The method of claim 1, wherein $HTNF_1$ or $HTNF_2$ has an amino acid sequence of SNYLYDN (SEQ ID NO:1) or HEXXH (SEQ ID NO:2), wherein each X is independently a basic amino acid residue.

3. The method of claim 1, wherein the other of $L_1$ or $L_2$ is a flexible linker, rigid linker, in vivo cleavable linker, or a combination thereof.

4. The method of claim 3, wherein the flexible linker is a hydrocarbon linker.

5. The method of claim 4, wherein the hydrocarbon linker has the structure —$(CH_2)_6$—.

6. The method of claim 3, wherein the flexible linker is a peptide linker having an amino acid sequence of $(GGGGS)_n$ (SEQ ID NO:3), KESGSVSSEQLAQFRSLD (SEQ ID NO:4), or EGKSSGSGSESKST (SEQ ID NO:5), GGGGGGGG (SEQ ID NO:6), GSAGSAAGSGEF (SEQ ID NO:7), $(GGSG)_n$ (SEQ ID NO:8), or $(GS)_n$ (SEQ ID NO:9), wherein n is 1, 2, 3, 4 or 5.

7. The method of claim 3, wherein the rigid linker is a peptide linker having an amino acid sequence of $(EAAAK)_n$ (SEQ ID NO:10), $A(EAAAK)_nA$ (SEQ ID NO:11), PAPAP (SEQ ID NO:12), or $(XP)_n$ (SEQ ID NO:13), wherein n is 1, 2, 3, 4 or 5.

8. The method of claim 3, wherein the in vivo cleavable linker is a peptide linker having an amino acid sequence of VSQTSKLTRAETVFPDV (SEQ ID NO:14), PLGLWA (SEQ ID NO:15), RVLAEA (SEQ ID NO:16), EDVVCCSMSY (SEQ ID NO:17), GGIEGRGS (SEQ ID NO:18), TRHRQPRGWE (SEQ ID NO:19), AGNRVRRSVG (SEQ ID NO:20), RRRRRRRRR (SEQ ID NO:21), GFLG (SEQ ID NO:22), or CRRRRRREAEAC (SEQ ID NO:23).

9. The method of claim 1, wherein said synthetic histatin is linear or cyclized.

10. The method of claim 9, wherein the synthetic histatin is cyclized via a disulfide bridge between terminal cysteine residues.

11. The method of claim 9, wherein the synthetic histatin is cyclized with a sortase or butelase.

12. The method of claim 1, wherein said synthetic histatin has the structure:

(a) GYKRKFHEKHHSHR(SEQ ID NO: 24)-$L_1$-YGDYGSNYLYDN (SEQ ID NO: 25);

(b) HEKHH(SEQ ID NO: 26)-$L_1$-HEKHH(SEQ ID NO: 26)-$L_2$-HEKHH(SEQ ID NO: 26)-$L_1$-YGDYGSNYLYDN(SEQ ID NO: 25);

-continued (c) HEKRHH(SEQ ID NO: 27)-$L_1$-HEKRHH(SEQ ID NO:27)-$L_2$-HEKRHH(SEQ ID NO: 27)-$L_1$-YGDYGSNYLYDN(SEQ ID NO: 25);

(d) HEKRHH(SEQ ID NO: 27)-$L_1$-HEKRHH(SEQ ID NO: 27)-$L_2$-HEKHH(SEQ ID NO: 26)-$L_1$-YGDYGSNYLYDN(SEQ ID NO: 25);
or (e) HEKRHH(SEQ ID NO: 27)-$L_1$-HEKHH(SEQ ID NO: 26)-$L_2$-HEKHH(SEQ ID NO: 26)-$L_1$-YGDYGSNYLYDN(SEQ ID NO: 25), wherein at least one of $L_1$ or $L_2$ is a hydrocarbon linker and the other of $L_1$ or $L_2$ is a flexible linker, rigid linker, or in vivo cleavable linker.

13. The method of claim 1, wherein said synthetic histatin has the structure:

(a) (SEQ ID NO: 28)
GYKRKFHEKHHSHR-$(CH_2)_6$-YGDYGSNYLYDN;

(b) (SEQ ID NO: 29)
HEKHH-$(CH_2)_6$-HEKHH-$(CH_2)_6$-HEKHH-$(CH_2)_6$-YGDYGSNYLYDN;

(c) (SEQ ID NO: 30)
HEKRHH-$(CH_2)_6$-HEKRHH-$(CH_2)_6$-HEKRHH-$(CH_2)_6$-YGDYGSNYLYDN;

(d) (SEQ ID NO: 31)
HEKRHH-$(CH_2)_6$-HEKRHH-$(CH_2)_6$-HEKHH-$(CH_2)_6$-YGDYGSNYLYDN;
or (e) (SEQ ID NO: 32)
HEKRHH-$(CH_2)_6$-HEKHH-$(CH_2)_6$-HEKHH-$(CH_2)_6$-YGDYGSNYLYDN

14. The method of claim 1, wherein the ocular disease or condition is an ocular surface inflammatory disorder, dry eye disease, ocular tissue neovascularization, age-related macular degeneration, diabetic retinopathy, chronic or acute severe uveitis, a retinal pigment epithelial disorder, an ocular surface disease, an infection, or corneal or conjunctival wound.

15. The method of claim 1, wherein the synthetic histatin provides wound healing, antimicrobial, metal ion chelating, anti-inflammatory, anti-angiogenic, or matrix metalloproteinase inhibitory activity.

16. A method of treating an ocular disease or condition comprising administering to a subject in need of treatment an effective amount of a synthetic histatin having the general structure:

$$[HTNF_1\text{-}L_1\text{-}HTNF_2\text{-}(L_2)_y]_x \quad \text{(Formula I)}$$

wherein i) $HTNF_1$ is a first histatin fragment ranging in length from 5 to 20 amino acids;

ii) $HTNF_2$ is a second histatin fragment ranging in length from 5 to 20 amino acids;

iii) $L_1$ is a first linker;

iv) $L_2$ is a second linker;

v) x=1 to 3; and vi) y=0 to 2;

wherein $HTNF_1$ and $HTNF_2$ are each independently the same or different and $L_1$ and $L_2$ are each independently the same or different, and wherein at least one of $HTNF_1$ or $HTNF_2$ is HEXXH (SEQ ID NO:2) or HEKRHH (SEQ ID NO:27), wherein each X is independently a basic amino acid residue, and wherein when each of $HTNF_1$ and $HTNF_2$ is HEHKH (SEQ ID NO:50), x is 1 and y is 0, thereby treating the subject's ocular disease or condition.

17. The method of claim 16, wherein $HTNF_1$ or $HTNF_2$ has an amino acid sequence of SNYLYDN (SEQ ID NO:1).

18. The method of claim 16, wherein $L_1$ or $L_2$ is a flexible linker, rigid linker, in vivo cleavable linker, or a combination thereof.

19. The method of claim 18, wherein the flexible linker is a hydrocarbon linker comprising 3 to 25 methylene groups.

20. The method of claim 19, wherein the hydrocarbon linker has the structure —$(CH_2)_6$—.

21. The method of claim 18, wherein the flexible linker is a peptide linker having an amino acid sequence of $(GGGGS)_n$ (SEQ ID NO:3), KESGSVSSEQLAQFRSLD (SEQ ID NO:4), or EGKSSGSGSESKST (SEQ ID NO:5), GGGGGGGG (SEQ ID NO:6), GSAGSAAGSGEF (SEQ ID NO:7), $(GGSG)_n$ (SEQ ID NO:8), or $(GS)_n$ (SEQ ID NO:9), wherein n is 1, 2, 3, 4 or 5.

22. The method of claim 18, wherein the rigid linker is a peptide linker having an amino acid sequence of $(EAAAK)_n$ (SEQ ID NO:10), $A(EAAAK)_nA$ (SEQ ID NO:11), PAPAP (SEQ ID NO:12), or $(XP)_n$ (SEQ ID NO:13), wherein n is 1, 2, 3, 4 or 5.

23. The method of claim 18, wherein the in vivo cleavable linker is a peptide linker having an amino acid sequence of VSQTSKLTRAETVFPDV (SEQ ID NO:14), PLGLWA (SEQ ID NO:15), RVLAEA (SEQ ID NO:16), EDVVCCSMSY (SEQ ID NO:17), GGIEGRGS (SEQ ID NO:18), TRHRQPRGWE (SEQ ID NO:19), AGNRVRRSVG (SEQ ID NO:20), RRRRRRRRR (SEQ ID NO:21), GFLG (SEQ ID NO:22), or CRRRRRREAEAC (SEQ ID NO:23).

24. The method of claim 16, wherein said synthetic histatin is linear or cyclized.

25. The method of claim 24, wherein the synthetic histatin is cyclized via a disulfide bridge between terminal cysteine residues.

26. The method of claim 24, wherein the synthetic histatin is cyclized with a sortase or butelase.

27. The method of claim 16, wherein the ocular disease or condition is an ocular surface inflammatory disorder, dry eye disease, ocular tissue neovascularization, age-related macular degeneration, diabetic retinopathy, chronic or acute severe uveitis, a retinal pigment epithelial disorder, an ocular surface disease, an infection, or corneal or conjunctival wound.

28. The method of claim 16, wherein the synthetic histatin provides wound healing, antimicrobial, metal ion chelating, anti-inflammatory, anti-angiogenic, or matrix metalloproteinase inhibitory activity.

* * * * *

SEQUENCE LISTING

```
<160> NUMBER OF SEQ ID NOS: 60

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Ser Asn Tyr Leu Tyr Asp Asn
1               5


<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(4)
<223> OTHER INFORMATION: Xaa denotes a basic amino acid residue.

<400> SEQUENCE: 2

His Glu Xaa Xaa His
1               5


<210> SEQ ID NO 3
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(9)
<223> OTHER INFORMATION: Xaa is present or absent and when present
      denotes Gly.
<220> FEATURE:
<221> NAME/KEY: MISC_FEATURE
<222> LOCATION: (10)..(10)
<223> OTHER INFORMATION: Xaa is present or absent and when present
      denotes Ser.
<220> FEATURE:
<221> NAME/KEY: MISC_FEATURE
<222> LOCATION: (11)..(14)
<223> OTHER INFORMATION: Xaa is present or absent and when present
      denotes Gly.
<220> FEATURE:
<221> NAME/KEY: MISC_FEATURE
<222> LOCATION: (15)..(15)
<223> OTHER INFORMATION: Xaa is present or absent and when present
      denotes Ser.
<220> FEATURE:
<221> NAME/KEY: MISC_FEATURE
<222> LOCATION: (16)..(19)
<223> OTHER INFORMATION: Xaa is present or absent and when present
      denotes Gly.
<220> FEATURE:
<221> NAME/KEY: MISC_FEATURE
<222> LOCATION: (20)..(20)
<223> OTHER INFORMATION: Xaa is present or absent and when present
      denotes Ser.
<220> FEATURE:
<221> NAME/KEY: MISC_FEATURE
<222> LOCATION: (21)..(24)
<223> OTHER INFORMATION: Xaa is present or absent and when present
      denotes Gly.
```

<220> FEATURE:
<221> NAME/KEY: MISC_FEATURE
<222> LOCATION: (25)..(25)
<223> OTHER INFORMATION: Xaa is present or absent and when present denotes Ser.

<400> SEQUENCE: 3

Gly Gly Gly Gly Ser Xaa Xaa Xaa Xaa Xaa Xaa Xaa Xaa Xaa Xaa Xaa
1 5 10 15

Xaa Xaa Xaa Xaa Xaa Xaa Xaa Xaa Xaa
20 25

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Lys Glu Ser Gly Ser Val Ser Ser Glu Gln Leu Ala Gln Phe Arg Ser
1 5 10 15

Leu Asp

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

<400> SEQUENCE: 5

Glu Gly Lys Ser Ser Gly Ser Gly Ser Glu Ser Lys Ser Thr
1 5 10

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Gly Gly Gly Gly Gly Gly Gly Gly
1 5

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Gly Ser Ala Gly Ser Ala Ala Gly Ser Gly Glu Phe
1 5 10

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(6)
<223> OTHER INFORMATION: Xaa is present or absent and when present

```
      denotes Gly.
<220> FEATURE:
<221> NAME/KEY: MISC_FEATURE
<222> LOCATION: (7)..(7)
<223> OTHER INFORMATION: Xaa is present or absent and when present
      denotes Ser.
<220> FEATURE:
<221> NAME/KEY: MISC_FEATURE
<222> LOCATION: (8)..(10)
<223> OTHER INFORMATION: Xaa is present or absent and when present
      denotes Gly.
<220> FEATURE:
<221> NAME/KEY: MISC_FEATURE
<222> LOCATION: (11)..(11)
<223> OTHER INFORMATION: Xaa is present or absent and when present
      denotes Ser.
<220> FEATURE:
<221> NAME/KEY: MISC_FEATURE
<222> LOCATION: (12)..(14)
<223> OTHER INFORMATION: Xaa is present or absent and when present
      denotes Gly.
<220> FEATURE:
<221> NAME/KEY: MISC_FEATURE
<222> LOCATION: (15)..(15)
<223> OTHER INFORMATION: Xaa is present or absent and when present
      denotes Ser.
<220> FEATURE:
<221> NAME/KEY: MISC_FEATURE
<222> LOCATION: (16)..(18)
<223> OTHER INFORMATION: Xaa is present or absent and when present
      denotes Gly.
<220> FEATURE:
<221> NAME/KEY: MISC_FEATURE
<222> LOCATION: (19)..(19)
<223> OTHER INFORMATION: Xaa is present or absent and when present
      denotes Ser.
<220> FEATURE:
<221> NAME/KEY: MISC_FEATURE
<222> LOCATION: (20)..(20)
<223> OTHER INFORMATION: Xaa is present or absent and when present
      denotes Gly.

<400> SEQUENCE: 8

Gly Gly Ser Gly Xaa Xaa Xaa Xaa Xaa Xaa Xaa Xaa Xaa Xaa Xaa Xaa
1               5                   10                  15

Xaa Xaa Xaa Xaa
            20


<210> SEQ ID NO 9
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is present or absent and when present
      denotes Gly.
<220> FEATURE:
<221> NAME/KEY: MISC_FEATURE
<222> LOCATION: (4)..(4)
<223> OTHER INFORMATION: Xaa is present or absent and when present
      denotes Ser.
<220> FEATURE:
<221> NAME/KEY: MISC_FEATURE
<222> LOCATION: (5)..(5)
<223> OTHER INFORMATION: Xaa is present or absent and when present
      denotes Gly.
<220> FEATURE:
<221> NAME/KEY: MISC_FEATURE
<222> LOCATION: (6)..(6)
<223> OTHER INFORMATION: Xaa is present or absent and when present
      denotes Ser.
<220> FEATURE:
<221> NAME/KEY: MISC_FEATURE
```

```
<222> LOCATION: (7)..(7)
<223> OTHER INFORMATION: Xaa is present or absent and when present
      denotes Gly.
<220> FEATURE:
<221> NAME/KEY: MISC_FEATURE
<222> LOCATION: (8)..(8)
<223> OTHER INFORMATION: Xaa is present or absent and when present
      denotes Ser.
<220> FEATURE:
<221> NAME/KEY: MISC_FEATURE
<222> LOCATION: (9)..(9)
<223> OTHER INFORMATION: Xaa is present or absent and when present
      denotes Gly.
<220> FEATURE:
<221> NAME/KEY: MISC_FEATURE
<222> LOCATION: (10)..(10)
<223> OTHER INFORMATION: Xaa is present or absent and when present
      denotes Ser.

<400> SEQUENCE: 9

Gly Ser Xaa Xaa Xaa Xaa Xaa Xaa Xaa Xaa
1               5                   10


<210> SEQ ID NO 10
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is present or absent and when present
      denotes Glu.
<220> FEATURE:
<221> NAME/KEY: MISC_FEATURE
<222> LOCATION: (7)..(9)
<223> OTHER INFORMATION: Xaa is present or absent and when present
      denotes Ala.
<220> FEATURE:
<221> NAME/KEY: MISC_FEATURE
<222> LOCATION: (10)..(10)
<223> OTHER INFORMATION: Xaa is present or absent and when present
      denotes Lys.
<220> FEATURE:
<221> NAME/KEY: MISC_FEATURE
<222> LOCATION: (11)..(11)
<223> OTHER INFORMATION: Xaa is present or absent and when present
      denotes Glu.
<220> FEATURE:
<221> NAME/KEY: MISC_FEATURE
<222> LOCATION: (12)..(14)
<223> OTHER INFORMATION: Xaa is present or absent and when present
      denotes Ala.
<220> FEATURE:
<221> NAME/KEY: MISC_FEATURE
<222> LOCATION: (15)..(15)
<223> OTHER INFORMATION: Xaa is present or absent and when present
      denotes Lys.
<220> FEATURE:
<221> NAME/KEY: MISC_FEATURE
<222> LOCATION: (16)..(16)
<223> OTHER INFORMATION: Xaa is present or absent and when present
      denotes Glu.
<220> FEATURE:
<221> NAME/KEY: MISC_FEATURE
<222> LOCATION: (17)..(19)
<223> OTHER INFORMATION: Xaa is present or absent and when present
      denotes Ala.
<220> FEATURE:
<221> NAME/KEY: MISC_FEATURE
<222> LOCATION: (20)..(20)
<223> OTHER INFORMATION: Xaa is present or absent and when present
      denotes Lys.
<220> FEATURE:
<221> NAME/KEY: MISC_FEATURE
<222> LOCATION: (21)..(21)
```

```
<223> OTHER INFORMATION: Xaa is present or absent and when present
      denotes Glu.
<220> FEATURE:
<221> NAME/KEY: MISC_FEATURE
<222> LOCATION: (22)..(24)
<223> OTHER INFORMATION: Xaa is present or absent and when present
      denotes Ala.
<220> FEATURE:
<221> NAME/KEY: MISC_FEATURE
<222> LOCATION: (25)..(25)
<223> OTHER INFORMATION: Xaa is present or absent and when present
      denotes Lys.

<400> SEQUENCE: 10

Glu Ala Ala Ala Lys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25


<210> SEQ ID NO 11
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is present or absent and when present
      denotes Glu.
<220> FEATURE:
<221> NAME/KEY: MISC_FEATURE
<222> LOCATION: (8)..(10)
<223> OTHER INFORMATION: Xaa is present or absent and when present
      denotes Ala.
<220> FEATURE:
<221> NAME/KEY: MISC_FEATURE
<222> LOCATION: (11)..(11)
<223> OTHER INFORMATION: Xaa is present or absent and when present
      denotes Lys.
<220> FEATURE:
<221> NAME/KEY: MISC_FEATURE
<222> LOCATION: (12)..(12)
<223> OTHER INFORMATION: Xaa is present or absent and when present
      denotes Glu.
<220> FEATURE:
<221> NAME/KEY: MISC_FEATURE
<222> LOCATION: (13)..(15)
<223> OTHER INFORMATION: Xaa is present or absent and when present
      denotes Ala.
<220> FEATURE:
<221> NAME/KEY: MISC_FEATURE
<222> LOCATION: (16)..(16)
<223> OTHER INFORMATION: Xaa is present or absent and when present
      denotes Lys.
<220> FEATURE:
<221> NAME/KEY: MISC_FEATURE
<222> LOCATION: (17)..(17)
<223> OTHER INFORMATION: Xaa is present or absent and when present
      denotes Glu.
<220> FEATURE:
<221> NAME/KEY: MISC_FEATURE
<222> LOCATION: (18)..(20)
<223> OTHER INFORMATION: Xaa is present or absent and when present
      denotes Ala.
<220> FEATURE:
<221> NAME/KEY: MISC_FEATURE
<222> LOCATION: (21)..(21)
<223> OTHER INFORMATION: Xaa is present or absent and when present
      denotes Lys.
<220> FEATURE:
<221> NAME/KEY: MISC_FEATURE
<222> LOCATION: (22)..(22)
<223> OTHER INFORMATION: Xaa is present or absent and when present
      denotes Glu.
<220> FEATURE:
```

```
<221> NAME/KEY: MISC_FEATURE
<222> LOCATION: (23)..(25)
<223> OTHER INFORMATION: Xaa is present or absent and when present
      denotes Ala.
<220> FEATURE:
<221> NAME/KEY: MISC_FEATURE
<222> LOCATION: (26)..(26)
<223> OTHER INFORMATION: Xaa is present or absent and when present
      denotes Lys.

<400> SEQUENCE: 11

Ala Glu Ala Ala Ala Lys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Ala
            20                  25


<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Pro Ala Pro Ala Pro
1               5


<210> SEQ ID NO 13
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes any amino acid residue.
<220> FEATURE:
<221> NAME/KEY: MISC_FEATURE
<222> LOCATION: (3)..(3)
<223> OTHER INFORMATION: Xaa is present or absent and when present
      denotes any amino acid residue.
<220> FEATURE:
<221> NAME/KEY: MISC_FEATURE
<222> LOCATION: (4)..(4)
<223> OTHER INFORMATION: Xaa is present or absent and when present
      denotes Pro.
<220> FEATURE:
<221> NAME/KEY: MISC_FEATURE
<222> LOCATION: (5)..(5)
<223> OTHER INFORMATION: Xaa is present or absent and when present
      denotes any amino acid residue.
<220> FEATURE:
<221> NAME/KEY: MISC_FEATURE
<222> LOCATION: (6)..(6)
<223> OTHER INFORMATION: Xaa is present or absent and when present
      denotes Pro.
<220> FEATURE:
<221> NAME/KEY: MISC_FEATURE
<222> LOCATION: (7)..(7)
<223> OTHER INFORMATION: Xaa is present or absent and when present
      denotes any amino acid residue.
<220> FEATURE:
<221> NAME/KEY: MISC_FEATURE
<222> LOCATION: (8)..(8)
<223> OTHER INFORMATION: Xaa is present or absent and when present
      denotes Pro.
<220> FEATURE:
<221> NAME/KEY: MISC_FEATURE
<222> LOCATION: (9)..(9)
<223> OTHER INFORMATION: Xaa is present or absent and when present
      denotes any amino acid residue.
<220> FEATURE:
<221> NAME/KEY: MISC_FEATURE
```

<222> LOCATION: (10)..(10)
<223> OTHER INFORMATION: Xaa is present or absent and when present denotes Pro.

<400> SEQUENCE: 13

Xaa Pro Xaa Xaa Xaa Xaa Xaa Xaa Xaa Xaa
1 5 10

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide

<400> SEQUENCE: 14

Val Ser Gln Thr Ser Lys Leu Thr Arg Ala Glu Thr Val Phe Pro Asp
1 5 10 15

Val

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Pro Leu Gly Leu Trp Ala
1 5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Arg Val Leu Ala Glu Ala
1 5

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Glu Asp Val Val Cys Cys Ser Met Ser Tyr
1 5 10

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Gly Gly Ile Glu Gly Arg Gly Ser
1 5

<210> SEQ ID NO 19
<211> LENGTH: 10

<212> TYPE: PRT
<213> ORGANISM: Artificial Sequence
<220> FEATURE:
<223> OTHER INFORMATION: Synthetic peptide

<400> SEQUENCE: 19

Thr Arg His Arg Gln Pro Arg Gly Trp Glu
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Gly Asn Arg Val Arg Arg Ser Val Gly
1 5 10

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

Arg Arg Arg Arg Arg Arg Arg Arg Arg
1 5

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Gly Phe Leu Gly
1

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Cys Arg Arg Arg Arg Arg Arg Glu Ala Glu Ala Cys
1 5 10

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide

<400> SEQUENCE: 24

Gly Tyr Lys Arg Lys Phe His Glu Lys His His Ser His Arg
1 5 10

<210> SEQ ID NO 25
<211> LENGTH: 12
<212> TYPE: PRT

```
<213> ORGANISM: Artificial Sequence
<220> FEATURE:
<223> OTHER INFORMATION: Synthetic peptide

<400> SEQUENCE: 25

Tyr Gly Asp Tyr Gly Ser Asn Tyr Leu Tyr Asp Asn
1               5                   10


<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

His Glu Lys His His
1               5


<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

His Glu Lys Arg His His
1               5


<210> SEQ ID NO 28
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (14)..(15)
<223> OTHER INFORMATION: Residues linked by -(CH2)6- hydrocarbon.

<400> SEQUENCE: 28

Gly Tyr Lys Arg Lys Phe His Glu Lys His His Ser His Tyr Gly Asp
1               5                   10                  15

Tyr Gly Ser Asn Tyr Leu Tyr Asp Asn
            20                  25


<210> SEQ ID NO 29
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (5)..(6)
<223> OTHER INFORMATION: Residues linked by -(CH2)6- hydrocarbon.
<220> FEATURE:
<221> NAME/KEY: NON_CONS
<222> LOCATION: (10)..(11)
<223> OTHER INFORMATION: Residues linked by -(CH2)6- hydrocarbon.
<220> FEATURE:
<221> NAME/KEY: NON_CONS
<222> LOCATION: (15)..(16)
<223> OTHER INFORMATION: Residues linked by -(CH2)6- hydrocarbon.

<400> SEQUENCE: 29

His Glu Lys His His His Glu Lys His His His Glu Lys His His Tyr
1               5                   10                  15
```

```
Gly Asp Tyr Gly Ser Asn Tyr Leu Tyr Asp Asn
            20                  25


<210> SEQ ID NO 30
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (6)..(7)
<223> OTHER INFORMATION: Residues linked by -(CH2)6- hydrocarbon.
<220> FEATURE:
<221> NAME/KEY: NON_CONS
<222> LOCATION: (12)..(13)
<223> OTHER INFORMATION: Residues linked by -(CH2)6- hydrocarbon.
<220> FEATURE:
<221> NAME/KEY: NON_CONS
<222> LOCATION: (18)..(19)
<223> OTHER INFORMATION: Residues linked by -(CH2)6- hydrocarbon.

<400> SEQUENCE: 30

His Glu Lys Arg His His His Glu Lys Arg His His His Glu Lys Arg
1               5                   10                  15

His His Tyr Gly Asp Tyr Gly Ser Asn Tyr Leu Tyr Asp Asn
            20                  25                  30


<210> SEQ ID NO 31
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (6)..(7)
<223> OTHER INFORMATION: Residues linked by -(CH2)6- hydrocarbon.
<220> FEATURE:
<221> NAME/KEY: NON_CONS
<222> LOCATION: (12)..(13)
<223> OTHER INFORMATION: Residues linked by -(CH2)6- hydrocarbon.
<220> FEATURE:
<221> NAME/KEY: NON_CONS
<222> LOCATION: (17)..(18)
<223> OTHER INFORMATION: Residues linked by -(CH2)6- hydrocarbon.

<400> SEQUENCE: 31

His Glu Lys Arg His His His Glu Lys Arg His His His Glu Lys His
1               5                   10                  15

His Tyr Gly Asp Tyr Gly Ser Asn Tyr Leu Tyr Asp Asn
            20                  25


<210> SEQ ID NO 32
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (6)..(7)
<223> OTHER INFORMATION: Residues linked by -(CH2)6- hydrocarbon.
<220> FEATURE:
<221> NAME/KEY: NON_CONS
<222> LOCATION: (11)..(12)
<223> OTHER INFORMATION: Residues linked by -(CH2)6- hydrocarbon.
<220> FEATURE:
<221> NAME/KEY: NON_CONS
<222> LOCATION: (16)..(17)
<223> OTHER INFORMATION: Residues linked by -(CH2)6- hydrocarbon.
```

```
<400> SEQUENCE: 32

His Glu Lys Arg His His His Glu Lys His His His Glu Lys His His
1               5                   10                  15

Tyr Gly Asp Tyr Gly Ser Asn Tyr Leu Tyr Asp Asn
            20                  25


<210> SEQ ID NO 33
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: PHOSPHORYLATION

<400> SEQUENCE: 33

Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
        35


<210> SEQ ID NO 34
<211> LENGTH: 27
<212> TYPE: PRT
<213> ORGANISM: Artificial Sequence
<220> FEATURE:
<223> OTHER INFORMATION: Synthetic peptide

<400> SEQUENCE: 34

Arg Lys Phe His Glu Lys His His Ser His Arg Glu Phe Pro Phe Tyr
1               5                   10                  15

Gly Asp Tyr Gly Ser Asn Tyr Leu Tyr Asp Asn
            20                  25


<210> SEQ ID NO 35
<211> LENGTH: 32
<212> TYPE: PRT
<213> ORGANISM: Artificial Sequence
<220> FEATURE:
<223> OTHER INFORMATION: Synthetic peptide

<400> SEQUENCE: 35

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30


<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Lys Phe His Glu Lys His His Ser His Arg Gly Tyr Arg Ser Asn Tyr
1               5                   10                  15

Leu Tyr Asp Asn
            20
```

```
<210> SEQ ID NO 37
<211> LENGTH: 24
<212> TYPE: PRT
<213> ORGANISM: Artificial Sequence
<220> FEATURE:
<223> OTHER INFORMATION: Synthetic peptide

<400> SEQUENCE: 37

Asp Ser His Ala Lys Arg His His Gly Tyr Lys Arg Lys Phe His Glu
1               5                   10                  15

Lys His His Ser His Arg Gly Tyr
            20


<210> SEQ ID NO 38
<211> LENGTH: 25
<212> TYPE: PRT
<213> ORGANISM: Artificial Sequence
<220> FEATURE:
<223> OTHER INFORMATION: Synthetic peptide

<400> SEQUENCE: 38

Asp Ser His Ala Lys Arg His His Gly Tyr Lys Arg Lys Phe His Glu
1               5                   10                  15

Lys His His Ser His Arg Gly Tyr Arg
            20                  25


<210> SEQ ID NO 39
<211> LENGTH: 13
<212> TYPE: PRT
<213> ORGANISM: Artificial Sequence
<220> FEATURE:
<223> OTHER INFORMATION: Synthetic peptide

<400> SEQUENCE: 39

Arg Lys Phe His Glu Lys His His Ser His Arg Gly Tyr
1               5                   10


<210> SEQ ID NO 40
<211> LENGTH: 12
<212> TYPE: PRT
<213> ORGANISM: Artificial Sequence
<220> FEATURE:
<223> OTHER INFORMATION: Synthetic peptide

<400> SEQUENCE: 40

Lys Phe His Glu Lys His His Ser His Arg Gly Tyr
1               5                   10


<210> SEQ ID NO 41
<211> LENGTH: 14
<212> TYPE: PRT
<213> ORGANISM: Artificial Sequence
<220> FEATURE:
<223> OTHER INFORMATION: Synthetic peptide

<400> SEQUENCE: 41

Arg Lys Phe His Glu Lys His His Ser His Arg Gly Tyr Arg
1               5                   10


<210> SEQ ID NO 42
<211> LENGTH: 13
<212> TYPE: PRT
<213> ORGANISM: Artificial Sequence
<220> FEATURE:
<223> OTHER INFORMATION: Synthetic peptide
```

<400> SEQUENCE: 42

Lys Phe His Glu Lys His His Ser His Arg Gly Tyr Arg
1 5 10

<210> SEQ ID NO 43
<211> LENGTH: 8
<212> TYPE: PRT
<213> ORGANISM: Artificial Sequence
<220> FEATURE:
<223> OTHER INFORMATION: Synthetic peptide

<400> SEQUENCE: 43

Lys Arg His His Gly Tyr Lys Arg
1 5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Lys Arg His His Gly Tyr Lys
1 5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

His Glu Lys Lys His
1 5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

His Glu Lys Arg His
1 5

<210> SEQ ID NO 47
<211> LENGTH: 5
<212> TYPE: PRT
<213> ORGANISM: Artificial Sequence
<220> FEATURE:
<223> OTHER INFORMATION: Synthetic peptide

<400> SEQUENCE: 47

His Glu Arg Lys His
1 5

<210> SEQ ID NO 48
<211> LENGTH: 5
<212> TYPE: PRT
<213> ORGANISM: Artificial Sequence
<220> FEATURE:
<223> OTHER INFORMATION: Synthetic peptide

<400> SEQUENCE: 48

His Glu Arg Arg His
1 5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

His Glu Arg His His
1 5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

His Glu His Lys His
1 5

<210> SEQ ID NO 51
<211> LENGTH: 5
<212> TYPE: PRT
<213> ORGANISM: Artificial Sequence
<220> FEATURE:
<223> OTHER INFORMATION: Synthetic peptide

<400> SEQUENCE: 51

His Glu His Arg His
1 5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

His Glu His His His
1 5

<210> SEQ ID NO 53
<211> LENGTH: 14
<212> TYPE: PRT
<213> ORGANISM: Artificial Sequence
<220> FEATURE:
<223> OTHER INFORMATION: Synthetic peptide

<400> SEQUENCE: 53

Arg Lys Phe His Glu Lys His His Ser His Arg Gly Tyr Arg
1 5 10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

```
Ala Lys Arg His His Gly Tyr Lys Arg Lys Phe His
1               5                   10


<210> SEQ ID NO 55
<211> LENGTH: 16
<212> TYPE: PRT
<213> ORGANISM: Artificial Sequence
<220> FEATURE:
<223> OTHER INFORMATION: Synthetic peptide

<400> SEQUENCE: 55

Arg Gln Ile Lys Ile Trp Phe Gln Asn Arg Arg Met Lys Trp Lys Lys
1               5                   10                  15


<210> SEQ ID NO 56
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (15)..(16)
<223> OTHER INFORMATION: Residues linked by -(CH2)6- hydrocarbon.

<400> SEQUENCE: 56

Cys Gly Tyr Lys Arg Lys Phe His Glu Lys His His Ser His Arg Tyr
1               5                   10                  15

Gly Asp Tyr Gly Ser Asn Tyr Leu Tyr Asp Asn Cys
            20                  25


<210> SEQ ID NO 57
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (6)..(7)
<223> OTHER INFORMATION: Residues linked by -(CH2)6- hydrocarbon.
<220> FEATURE:
<221> NAME/KEY: NON_CONS
<222> LOCATION: (11)..(12)
<223> OTHER INFORMATION: Residues linked by -(CH2)6- hydrocarbon.
<220> FEATURE:
<221> NAME/KEY: NON_CONS
<222> LOCATION: (16)..(17)
<223> OTHER INFORMATION: Residues linked by -(CH2)6- hydrocarbon.

<400> SEQUENCE: 57

Cys His Glu Lys His His His Glu Lys His His His Glu Lys His His
1               5                   10                  15

Tyr Gly Asp Tyr Gly Ser Asn Tyr Leu Tyr Asp Asn Cys
            20                  25


<210> SEQ ID NO 58
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (7)..(8)
<223> OTHER INFORMATION: Residues linked by -(CH2)6- hydrocarbon.
<220> FEATURE:
<221> NAME/KEY: NON_CONS
<222> LOCATION: (13)..(14)
```

<223> OTHER INFORMATION: Residues linked by -(CH2)6- hydrocarbon.
<220> FEATURE:
<221> NAME/KEY: NON_CONS
<222> LOCATION: (19)..(20)
<223> OTHER INFORMATION: Residues linked by -(CH2)6- hydrocarbon.

<400> SEQUENCE: 58

```
Cys His Glu Lys Arg His His His Glu Lys Arg His His His Glu Lys
1               5                   10                  15

Arg His His Tyr Gly Asp Tyr Gly Ser Asn Tyr Leu Tyr Asp Asn Cys
            20                  25                  30
```

<210> SEQ ID NO 59
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(8)
<223> OTHER INFORMATION: Residues linked by -(CH2)6- hydrocarbon.
<220> FEATURE:
<221> NAME/KEY: MISC_FEATURE
<222> LOCATION: (13)..(14)
<223> OTHER INFORMATION: Residues linked by -(CH2)6- hydrocarbon.
<220> FEATURE:
<221> NAME/KEY: MISC_FEATURE
<222> LOCATION: (18)..(19)
<223> OTHER INFORMATION: Residues linked by -(CH2)6- hydrocarbon.

<400> SEQUENCE: 59

```
Cys His Glu Lys Arg His His His Glu Lys Arg His His His Glu Lys
1               5                   10                  15

His His Tyr Gly Asp Tyr Gly Ser Asn Tyr Leu Tyr Asp Asn Cys
            20                  25                  30
```

<210> SEQ ID NO 60
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (7)..(8)
<223> OTHER INFORMATION: Residues linked by -(CH2)6- hydrocarbon.
<220> FEATURE:
<221> NAME/KEY: NON_CONS
<222> LOCATION: (12)..(13)
<223> OTHER INFORMATION: Residues linked by -(CH2)6- hydrocarbon.
<220> FEATURE:
<221> NAME/KEY: NON_CONS
<222> LOCATION: (17)..(18)
<223> OTHER INFORMATION: Residues linked by -(CH2)6- hydrocarbon.

<400> SEQUENCE: 60

```
Cys His Glu Lys Arg His His His Glu Lys His His His Glu Lys His
1               5                   10                  15

His Tyr Gly Asp Tyr Gly Ser Asn Tyr Leu Tyr Asp Asn Cys
            20                  25                  30
```